(12) United States Patent
Palmer et al.

(10) Patent No.: US 10,370,422 B2
(45) Date of Patent: Aug. 6, 2019

(54) MEMBRANE-ANCHORING AND APOPTOSIS-INDUCING FUSION PROTEIN COMPRISING A FRAGMENT OF TRAIL AND CD40L AND ENCODING POLYNUCLEOTIDES

(71) Applicant: The University of Liverpool, Liverpool (GB)

(72) Inventors: Daniel Palmer, Liverpool (GB); Taha Elmitwalli, Liverpool (GB)

(73) Assignee: The University of Liverpool, Liverpool (GB)

( * ) Notice: Subject to any disclaimer, the term of this patent is extended or adjusted under 35 U.S.C. 154(b) by 0 days.

(21) Appl. No.: 15/304,282

(22) PCT Filed: Apr. 15, 2015

(86) PCT No.: PCT/GB2015/051145
§ 371 (c)(1),
(2) Date: Oct. 14, 2016

(87) PCT Pub. No.: WO2015/159079
PCT Pub. Date: Oct. 22, 2015

(65) Prior Publication Data
US 2017/0044226 A1 Feb. 16, 2017

(30) Foreign Application Priority Data
Apr. 15, 2014 (GB) .................................. 1406705.2

(51) Int. Cl.
*C07K 14/52* (2006.01)
*C07K 19/00* (2006.01)
(Continued)

(52) U.S. Cl.
CPC .... *C07K 14/4747* (2013.01); *C07K 14/70575* (2013.01); *C07K 2319/00* (2013.01); *C07K 2319/03* (2013.01)

(58) Field of Classification Search
None
See application file for complete search history.

(56) References Cited

U.S. PATENT DOCUMENTS 7,964,712 B2 * 6/2011 Prussak ................ C07K 14/525
435/252.3
9,221,895 B2 * 12/2015 Tykocinski ...... C07K 14/70575
(Continued)

FOREIGN PATENT DOCUMENTS

| CN | 1367248 A | 9/2002 |
|---|---|---|
| WO | WO2003/050254 | 6/2003 |
| WO | WO2013/098755 | 7/2013 |

OTHER PUBLICATIONS

Qusty, N., The TRAIL Pathway in Carcinomas; Regulation of Apoptosis and Therapeutic Application. Ph. D. Thesis, Univ. Birmingham, Feb. 2013.*

(Continued)

*Primary Examiner* — Claire Kaufman
(74) *Attorney, Agent, or Firm* — Faegre Baker Daniels LLP

(57) ABSTRACT

Provided are compositions comprising fusion proteins, polynucleotides and/or expression vectors with therapeutic utility for suppressing and/or treating cancer, as well as medical uses of these agents, and methods of treatment in which they are used. A fusion protein of the invention comprises an amino acid sequence that provides the apoptosis-inducing activity of TRAIL, and a membrane-anchoring amino acid sequence. The amino acid sequence that provides the apoptosis-inducing activity of TRAIL comprises the extracellular domain of TRAIL, or a fragment or variant thereof. A fusion (Continued)

protein comprising an amino acid sequence from TRAIL that is able to induce apoptosis, and a second sequence that anchors the first sequence to the cell membrane, is markedly more effective at reducing viability of TRAIL receptor positive cells than the naturally occurring ("wild type") TRAIL protein itself.

8 Claims, 15 Drawing Sheets

Specification includes a Sequence Listing.

(51) Int. Cl.
    *C12N 15/11*     (2006.01)
    *C07K 14/47*     (2006.01)
    *C07K 14/705*   (2006.01)

(56) References Cited

U.S. PATENT DOCUMENTS

2005/0244370 A1   11/2005   Pfizenmaier
2013/0302270 A1   11/2013   Spitzer et al.

OTHER PUBLICATIONS

T.E. Creighton, Proteins: Structures and molecular principles, (W.H. Freeman & Co.:New York), pp. 223-227,1984.*
Kametaka et al., REduction of CTLL-2 cytotoxicity by induction of apoptosis with a Fas-estrogen receptor chimera, Canc. Sci. 94: 639-643, 2003.*
Wiley et al., Identification and characterization of a new member of the TNF family that induces apoptosis, Immunity, 3:673-682, Dec. 1995.*
Armitage et al., Molecullar and biological characterization of a murine ligand for CD40, Nature, 357: 80-82, May 1992.*
Clarke et al., Reovirus-induced apoptosis is meidated by TRAIL, J. Viol. 74(17):8135-8139, Sep. 200.*
Pitti et al., Induction of apoptosis by Apo-2 ligand, a new member of the tumor necrosis factor cytokine family, J. Biol. Chem. 271(22):12687-12690, May 31, 1996.*
Almasan A et al: "APO2/TRAIL: Apoptosis Signaling, Biology, and Potential for Cancer Therapy", Cytokine and Growth Factor Reviews, Elsevier Ltd, GB, vol. 14, No. 3/04, Jan. 1, 2003, pp. 337-348.
Berg D et al: "Enforced covalent trimerization increases the activity of the TNF ligand family members TRAIL and CD95L", Cell Death and Differentiation, Nature Publishing Group, GB, vol. 14, No. 12, Dec. 1, 2007, pp. 2022-2034.
Bremer Edwin et al: "Target cell-restricted and -enhanced apoptosis induction by a scFv:sTRAIL fusion protein with specificity for the pancarcinoma-associated antigen EGP2", International Journal of Cancer, John Wiley & Sons, Inc, US, vol. 109, No. 2, Mar. 20, 2004, pp. 281-290.
Bremer Edwin et al: "Target cell-restricted apoptosis induction of acute leukemic T cells by a recombinant tumor necrosis factor-related apoptosis-inducing ligand fusion protein with specificity for human CD7", Cancer Research, American Association for Cancer Research, US, vol. 65, No. 8, Apr. 1, 2005, pp. 3380-3388.

Fan Qiu et al: "Annexin V-TRAIL fusion protein is a more sensitive and potent apoptotic inducer for cancer therapy", Scientific Reports, vol. 3, Dec. 20, 2013, pp. 1-9.
Gunjal Garg et al: "Novel treatment option for MUC16-positive malignancies with the targeted TRAIL-based fusion protein Meso-TR3", BMC Cancer, Biomed Central, London, GB, vol. 14, No. 1, Jan. 21, 2014, pp. 1-12.
H. Wang et al: "Immunoglobulin Fc Domain Fusion to TRAIL Significantly Prolongs Its Plasma Half-Life and Enhances Its Antitumor Activity", Molecular Cancer Therapeutics, vol. 13, No. 3, Jan. 15, 2014, pp. 4101-4106.
Harald Wajant et al: "Differential activation of TRAIL-R1 and -2 by soluble and membrane TRAIL allows selective surface antigen-directed activation of TRAIL-R2 by a soluble TRAIL derivative", Jan. 1, 2001, pp. 4101-4106.
Ja Young Seol et al: "Adenovirus-TRAIL can overcome TRAIL resistance and induce a bystander effect", Cancer Gene Therapy, vol. 10, No. 7, Jul. 1, 2003, pp. 540-548.
Luis Martinez-Lostao et al: "Liposome-bound APO2L/TRAIL is an effective treatment in a rabbit model of rheumatoid arthritis", Arthritis & Rheumatism, vol. 62, No. 8, Apr. 9, 2010, pp. 2272-2282.
Lyse Norian et al: "Advances in Viral Vector-Based TRAIL Gene Therapy for Cancer", Cancers, vol. 3, No. 4, Feb. 10, 2011, pp. 602-620.
M El-Mesery et al: "CD40-directed scFv-TRAIL fusion proteins induce CD40-restricted tumor cell death and activate dendritic cells", Cell Death and Disease, vol. 4, No. 11, Nov. 14, 2013, pp. 1-10.
M. De Bruyn et al: "Cell Surface Delivery of TRAIL Strongly Augments the Tumoricidal Activity of T Cells", Clinical Cancer Research, vol. 17, No. 17, Jul. 13, 2011, pp. 5625-5637.
M. J. Mitchell et al: "TRAIL-coated leukocytes that kill cancer cells in the circulation", Proceedings of the National Academy of Sciences, vol. 111, No. 3, Jan. 6, 2014, pp. 930-935.
Michael A. Sheard et al: "Membrane-bound TRAIL Supplements Natural Killer Cell Cytotoxicity Against Neuroblastoma Cells", Journal of Immunotherapy, vol. 36, No. 5, Jun. 1, 2013, pp. 318-329.
Van Der Sloot A M et al: "Designed TRAIL variants initiating apoptosis exclusively via the DR5 receptor", Proceedings of the National Academy of Sciences, National Academy of Sciences, US, vol. 103, No. 23, Jun. 6, 2006, pp. 8634-8639.
International Search Report and Written Opinion issued by the International Searching Authority in PCT/GB2015/051145 dated Oct. 22, 2015, all pages.
Combined Search and examination Report under Sections 17 and 18(3) in GB1406705.2, dated Mar. 31, 2015, pp. 1-6.
Seifert et al., Bioconjugate Chemistry 25 (2014), 'Immuno-LipoTRAIL: Targeted Delivery of TRAIL-Functionalized Liposomal Nanoparticles', pp. 879-887.
Pieczykolan et al., 'European Journal of Cancer 49 (S2) (2013), Abstract 46 The AD-056.9-Fusion of TRAIL/Apo2L with a membrane permeable peptide as a novel anticancer therapeutic,' Sep. 2013, p. S108.
Brunyn et al., Cancer Letters 332 (2013), 'Antibody-based fusion proteins to target death receptors in cancer,' May 6, 2010, pp. 175-183.

* cited by examiner

|        |     128   131      |              |
|--------|--------------------|--------------|
| FasL:  | SSL EKQI GHPSP | SEQ ID NO: 18 |
|        |     110   116      |              |
| CD40L: | EN SFEMQK G DQN | SEQ ID NO: 19 |
|        |     105   107      |              |
| TRAIL: | Q EKQ Q HISPL  | SEQ ID NO: 20 |

FIG. 11

SEQUENCE LISTING

<160> NUMBER OF SEQ ID NOS: 20

<210> SEQ ID NO 1
<211> LENGTH: 281
<212> TYPE: PRT
<213> ORGANISM: Homo sapiens

<400> SEQUENCE: 1

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190
```

Gln Glu Glu Ile Lys Glu Asn Thr Lys Asn Asp Lys Gln Met Val Gln
                195                 200                 205

Tyr Ile Tyr Lys Tyr Thr Ser Tyr Pro Asp Pro Ile Leu Leu Met Lys
        210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
        260                 265                 270

Ser Phe Phe Gly Ala Phe Leu Val Gly
                275                 280

<210> SEQ ID NO 2
<211> LENGTH: 261
<212> TYPE: PRT
<213> ORGANISM: Homo sapiens

<400> SEQUENCE: 2

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
                210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 3
<211> LENGTH: 276
<212> TYPE: PRT
<213> ORGANISM: Artificial Sequence
<220> FEATURE:
<223> OTHER INFORMATION: CD40L/TRAIL fusion protein

<400> SEQUENCE: 3

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Val Arg Glu Arg
            100                 105                 110

Gly Pro Gln Arg Val Ala Ala His Ile Thr Gly Thr Arg Gly Arg Ser
        115                 120                 125

Asn Thr Leu Ser Ser Pro Asn Ser Lys Asn Glu Lys Ala Leu Gly Arg
    130                 135                 140

Lys Ile Asn Ser Trp Glu Ser Ser Arg Ser Gly His Ser Phe Leu Ser
145                 150                 155                 160

Asn Leu His Leu Arg Asn Gly Glu Leu Val Ile His Glu Lys Gly Phe
                165                 170                 175

Tyr Tyr Ile Tyr Ser Gln Thr Tyr Phe Arg Phe Gln Glu Glu Ile Lys
            180                 185                 190

Glu Asn Thr Lys Asn Asp Lys Gln Met Val Gln Tyr Ile Tyr Lys Tyr
        195                 200                 205

Thr Ser Tyr Pro Asp Pro Ile Leu Leu Met Lys Ser Ala Arg Asn Ser
    210                 215                 220

Cys Trp Ser Lys Asp Ala Glu Tyr Gly Leu Tyr Ser Ile Tyr Gln Gly
225                 230                 235                 240

Gly Ile Phe Glu Leu Lys Glu Asn Asp Arg Ile Phe Val Ser Val Thr
                245                 250                 255

Asn Glu His Leu Ile Asp Met Asp His Glu Ala Ser Phe Phe Gly Ala
            260                 265                 270

Phe Leu Val Gly
        275
```

<210> SEQ ID NO 4
<211> LENGTH: 831
<212> TYPE: DNA
<213> ORGANISM: Artificial Sequence
<220> FEATURE:
<223> OTHER INFORMATION: Nucleotide sequence encoding the CD40L/TRAIL
      fusion protein

<400> SEQUENCE: 4

```
atgatcgaaa catacaacca aacttctccc cgatctgcgg ccactggact gcccatcagc      60
atgaaaattt ttatgtattt acttactgtt tttcttatca cccagatgat tgggtcagca     120 cttttttgctg tgtatcttca tagaaggttg gacaagatag aagatgaaag gaatcttcat    180
```

```
gaagattttg tattcatgaa acgatacag agatgcaaca caggagaaag atccttatcc      240
ttactgaact gtgaggagat taaaagccag tttgaaggct tgtgaagga tataatgtta      300 aacaaagagg agacgaagaa agaagtgaga gaaagaggtc ctcagagagt agcagctcac      360
ataactggga ccagaggaag aagcaacaca ttgtcttctc caaactccaa gaatgaaaag      420
gctctgggcc gcaaaataaa ctcctgggaa tcatcaagga gtgggcattc attcctgagc      480
aacttgcact tgaggaatgg tgaactggtc atccatgaaa aagggtttta ctacatctat      540
tcccaaacat actttcgatt tcaggaggaa ataaagaaa cacaaagaa cgacaaacaa      600 atggtccaat atatttacaa atacacaagt tatcctgacc ctatattgtt gatgaaaagt      660
gctagaaata gttgttggtc taaagatgca gaatatggac tctattccat ctatcaaggg      720
ggaatatttg agcttaagga aaatgacaga attttttgttt ctgtaacaaa tgagcacttg      780
atagacatgg accatgaagc cagttttttc ggggcctttt tagttggcta a              831

<210> SEQ ID NO 5
<211> LENGTH: 508
<212> TYPE: DNA
<213> ORGANISM: Homo sapiens

<400> SEQUENCE: 5
agtgagagaa agaggtcctc agagagtagc agctcacata actgggacca gaggaagaag      60
caacacattg tcttctccaa actccaagaa tgaaaaggct ctgggccgca aaataaactc      120 ctggaatca tcaaggagtg gcattcatt cctgagcaac ttgcacttga ggaatggtga      180
actggtcatc catgaaaaag gttttacta catctattcc caaacatact ttcgatttca      240
ggaggaaata aagaaaaca caagaacga caaacaaatg gtccaatata tttacaaata      300
cacaagttat cctgacccta tattgttgat gaaaagtgct agaaatagtt gttggtctaa      360
agatgcagaa tatggactct attccatcta tcaaggggga atatttgagc ttaaggaaaa      420
tgacagaatt tttgtttctg taacaaatga gcacttgata gacatggacc atgaagccag      480
ttttttttgg gcctttttag ttggctaa                                        508

<210> SEQ ID NO 6
<211> LENGTH: 508
<212> TYPE: DNA
<213> ORGANISM: Artificial Sequence
<220> FEATURE:
<223> OTHER INFORMATION: TRAIL sequence used in the fusion protein

<400> SEQUENCE: 6
agtgagagaa agaggtcctc agagagtagc agctcacata actgggacca gaggaagaag      60
caacacattg tcttctccaa actccaagaa tgaaaaggct ctgggccgca aaataaactc      120 ctggaatca tcaaggagtg gcattcatt cctgagcaac ttgcacttga ggaatggtga      180
actggtcatc catgaaaaag gttttacta catctattcc caaacatact ttcgatttca      240
ggaggaaata aagaaaaca caagaacga caaacaaatg gtccaatata tttacaaata      300
cacaagttat cctgacccta tattgttgat gaaaagtgct agaaatagtt gttggtctaa      360
agatgcagaa tatggactct attccatcta tcaaggggga atatttgagc ttaaggaaaa      420
tgacagaatt tttgtttctg taacaaatga gcacttgata gacatggacc atgaagccag      480
ttttttcggg gcctttttag ttggctaa                                        508

<210> SEQ ID NO 7
```

```
<211> LENGTH: 168
<212> TYPE: PRT
<213> ORGANISM: Homo sapiens

<400> SEQUENCE: 7

Val Arg Glu Arg Gly Pro Gln Arg Val Ala His Ile Thr Gly Thr
1               5                   10                  15

Arg Gly Arg Ser Asn Thr Leu Ser Ser Pro Asn Ser Lys Asn Glu Lys
                20                  25                  30

Ala Leu Gly Arg Lys Ile Asn Ser Trp Glu Ser Ser Arg Ser Gly His
            35                  40                  45

Ser Phe Leu Ser Asn Leu His Leu Arg Asn Gly Glu Leu Val Ile His
        50                  55                  60

Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly
                165

<210> SEQ ID NO 8
<211> LENGTH: 6
<212> TYPE: PRT
<213> ORGANISM: Artificial Sequence
<220> FEATURE:
<223> OTHER INFORMATION: Sequence recognized by N-myristoyl transferase
<220> FEATURE:
<221> NAME/KEY: misc_feature
<222> LOCATION: (3)..(5)
<223> OTHER INFORMATION: Xaa can be any naturally occurring amino acid

<400> SEQUENCE: 8

Met Gly Xaa Xaa Xaa Ser
1               5

<210> SEQ ID NO 9
<211> LENGTH: 6
<212> TYPE: PRT
<213> ORGANISM: Artificial Sequence
<220> FEATURE:
<223> OTHER INFORMATION: Sequence recognized by N-myristoyl transferase
<220> FEATURE:
<221> NAME/KEY: misc_feature
<222> LOCATION: (3)..(5)
<223> OTHER INFORMATION: Xaa can be any naturally occurring amino acid

<400> SEQUENCE: 9

Met Gly Xaa Xaa Xaa Thr
1               5

<210> SEQ ID NO 10
<211> LENGTH: 27
<212> TYPE: DNA
<213> ORGANISM: Artificial Sequence
<220> FEATURE:
```

```
<223> OTHER INFORMATION: CD40L1Sal1F Primer

<400> SEQUENCE: 10
agtcgacatg atcgaaacat acaacca                                                    27

<210> SEQ ID NO 11
<211> LENGTH: 24
<212> TYPE: DNA
<213> ORGANISM: Artificial Sequence
<220> FEATURE:
<223> OTHER INFORMATION: CD40L324R Primer

<400> SEQUENCE: 11
ttctttcttc gtctcctctt tgtt                                                       24

<210> SEQ ID NO 12
<211> LENGTH: 61
<212> TYPE: DNA
<213> ORGANISM: Artificial Sequence
<220> FEATURE:
<223> OTHER INFORMATION: pcDNATRAIL construct together with a forward
      CD40L324TRAIL340F primer

<400> SEQUENCE: 12
tataatgtta acaaagagg agacgaagaa agaagtgaga gaaagaggtc ctcagagagt                 60
a                                                                                61

<210> SEQ ID NO 13
<211> LENGTH: 26
<212> TYPE: DNA
<213> ORGANISM: Artificial Sequence
<220> FEATURE:
<223> OTHER INFORMATION: TRAIL846 HindIIIR primer

<400> SEQUENCE: 13
aaagctttta gccaactaaa aaggcc                                                     26

<210> SEQ ID NO 14
<211> LENGTH: 4
<212> TYPE: PRT
<213> ORGANISM: Artificial Sequence
<220> FEATURE:
<223> OTHER INFORMATION: FasL cleavage site

<400> SEQUENCE: 14

Glu Lys Gln Ile
1

<210> SEQ ID NO 15
<211> LENGTH: 7
<212> TYPE: PRT
<213> ORGANISM: Artificial Sequence
<220> FEATURE:
<223> OTHER INFORMATION: CD40L cleavage site

<400> SEQUENCE: 15

Ser Phe Glu Met Gln Lys Gly
1               5

<210> SEQ ID NO 16
<211> LENGTH: 4
<212> TYPE: PRT
<213> ORGANISM: Artificial Sequence
<220> FEATURE:
<223> OTHER INFORMATION: TRAIL fragment similar to the FasL cleavage
      site
```

```
<400> SEQUENCE: 16

Glu Lys Gln Gln
1

<210> SEQ ID NO 17
<211> LENGTH: 10
<212> TYPE: PRT
<213> ORGANISM: Artificial Sequence
<220> FEATURE:
<223> OTHER INFORMATION: TRAIL mutant 2 deletion

<400> SEQUENCE: 17

Glu Lys Gln Gln His Ile Ser Pro Leu Val
1               5                   10

<210> SEQ ID NO 18
<211> LENGTH: 12
<212> TYPE: PRT
<213> ORGANISM: Artificial Sequence
<220> FEATURE:
<223> OTHER INFORMATION: FasL fragment

<400> SEQUENCE: 18

Ser Ser Leu Glu Lys Gln Ile Gly His Pro Ser Pro
1               5                   10

<210> SEQ ID NO 19
<211> LENGTH: 12
<212> TYPE: PRT
<213> ORGANISM: Artificial Sequence
<220> FEATURE:
<223> OTHER INFORMATION: CD40L fragment

<400> SEQUENCE: 19

Glu Asn Ser Phe Glu Met Gln Lys Gly Asp Gln Asn
1               5                   10

<210> SEQ ID NO 20
<211> LENGTH: 10
<212> TYPE: PRT
<213> ORGANISM: Artificial Sequence
<220> FEATURE:
<223> OTHER INFORMATION: TRAIL fragment

<400> SEQUENCE: 20

Gln Glu Lys Gln Gln His Ile Ser Pro Leu
1               5                   10
```

MEMBRANE-ANCHORING AND APOPTOSIS-INDUCING FUSION PROTEIN COMPRISING A FRAGMENT OF TRAIL AND CD40L AND ENCODING POLYNUCLEOTIDES

CROSS-REFERENCE TO RELATED APPLICATIONS

This application is a U.S. National Phase filing of PCT/GB2015/051145, filed Apr. 15, 2015, which claims the benefit of Great Britain Application No. 1406705.2, filed Apr. 15, 2014, the entire disclosures of both are hereby expressly incorporated by reference herein in their entireties.

The present invention relates to fusion proteins, polynucleotides encoding such fusion proteins, and expression vectors comprising such polynucleotides. The fusion proteins, polynucleotides and expression vectors may have therapeutic utility, particularly in the prevention and/or treatment of cancer, and the invention also relates to medical uses of these agents, and methods of treatment in which they are used.

INTRODUCTION

Cancer is one of the leading causes of mortality worldwide, and was responsible for approximately 13% of all human deaths in 2007. As the global population ages, mortality caused by cancer is expected to increase.

There is a clinical wish to develop targeted therapies that allow the selective killing of cancer cells, unlike chemotherapy or radiotherapy, both of which non-specifically kill cells of many types. Targeted therapies will allow the amount of non-specific cell death associated with treatment to be reduced, thus enhancing efficacy and giving rise to improved drug safety profiles.

TNF-Related Apoptosis-Inducing Ligand (TRAIL) is a death receptor ligand, a family of type II transmembrane proteins that signal to target cells on cell-cell contact or after protease-mediated release into the extracellular space. Soluble forms of TRAIL have recently been investigated as potential anti-cancer agents. The amino acid sequence of TRAIL is set out in SEQ ID NO: 1.

CD40 ligand (CD40L), also known as CD154, is a member of the tumour necrosis factor (TNF) superfamily of molecules. As its name implies, it binds to CD40 on antigen presenting cells. The amino acid sequence of CD40L is set out in SEQ ID NO: 2.

SUMMARY OF THE INVENTION

In a first aspect, the invention provides a fusion protein comprising an amino acid sequence that provides the apoptosis-inducing activity of TRAIL, and a membrane-anchoring amino acid sequence.

In a second aspect the invention provides a polynucleotide encoding a fusion protein according to the first aspect of the invention.

In a third aspect the invention provides an expression vector comprising a polynucleotide in accordance with the second aspect of the invention.

The invention also provides medical uses of the fusion proteins, polynucleotides, and expression vectors of the first, second, and third aspects of the invention. These agents are particularly useful as medicaments in the prevention and/or treatment of cancer.

In a fourth aspect the invention provides a pharmaceutical composition comprising an expression vector in accordance with the third aspect of the invention.

In a fifth aspect the invention provides a method of preventing and/or treating cancer, the method comprising providing to a subject in need of such treatment a therapeutically effective amount of a fusion protein in accordance with the first aspect of the invention.

In a sixth aspect the invention provides a method of preventing and/or treating cancer, the method comprising providing to a subject in need of such treatment an expression vector in accordance with the third aspect of the invention.

The present invention is based upon the inventors' surprising finding that a fusion protein comprising an amino acid sequence from TRAIL that is able to induce apoptosis, and a second sequence that anchors the first sequence to the cell membrane, is markedly more effective at reducing viability of TRAIL receptor positive cells than the naturally occurring ("wild type") TRAIL protein itself.

Particularly effective in this regard is an exemplary fusion protein (set out in SEQ ID NO: 3) in which the extracellular domain of TRAIL is combined with the transmembrane domain of CD40L. There have been no previous disclosures to suggest the particular effectiveness of this novel fusion protein.

The approach that has been adopted by the inventors, exemplified by their development of fusion proteins of the invention comprising amino acid sequences from TRAIL and CD40L, contrasts with previous, unsupported suggestions, that efficacy of proteins such as TRAIL and CD40L may be improved by inhibiting cleavage of the membrane bound ligand through the disruption of internal protease cleavage sites. In fact, as described in more detail in the Examples section below, strategies directed towards the development of TRAIL derivatives in which endogenous cleavage sites are remove by mutation have proved to be unsuccessful. In contrast, the inventors' approach using fusion proteins is significantly more effective than the use of wild type TRAIL, wild type CD40L, or soluble TRAIL or CD40L.

The "Useful definitions" and "Detailed description of the invention" sections that follow provide, more details of further aspects of the invention, and preferred embodiments of the various aspects. Further details of the studies illustrating the benefits of the fusion proteins of the invention are described in the "Examples" section below.

Useful Definitions

Certain terms used herein will now be further defined in order to further facilitate the understanding of the present invention.

"Fusion Protein"

In accordance with its normal use, a fusion protein is taken to be a protein that comprises all or part of at least two naturally occurring proteins. It will be appreciated that naturally occurring proteins themselves do not meet this definition, and so a naturally occurring protein cannot be considered to constitute a "fusion protein" in accordance with the present invention. Thus, it may be preferred that if the amino acid sequence that provides the apoptosis-inducing activity of TRAIL consists of a sequence found in TRAIL, then membrane-anchoring amino acid sequence should not consist of the transmembrane region of TRAIL.

For the avoidance of doubt, a protein that essentially consists of sequence from a single naturally occurring protein, with the incorporation of some amino acid substitutions or dilutions, but without the introduction of amino acid sequences from a second naturally occurring protein, does not constitute a fusion protein within the meaning of the present invention.

"Amino Acid Sequence that Provides the Apoptosis-Inducing Activity of TRAIL"

An "amino acid sequence that provides the apoptosis-inducing activity of TRAIL" is, for the purposes of the present invention any amino acid sequence that is capable of exerting the ability to induce apoptosis observed in respect of TRAIL.

The skilled person will readily be able to determine whether or not a sequence provides this activity, and in connection with this may consider whether or not the sequence is able to induce apoptosis, whether such apoptosis is induced only in cells that express TRAIL-R1 and/or TRAIL-R2, and whether the ability to induce apoptosis in this manner is inhibited by the presence of either neutralizing antibodies to TRAIL, or soluble TRAIL. Suitable assays by which the ability of an amino acid sequence to provide the apoptosis-inducing activity of TRAIL may be investigated are discussed further in the Examples section.

In a suitable embodiment, the amino acid sequence that provides the apoptosis-inducing activity of TRAIL comprises the extracellular domain of TRAIL, or a fragment or variant thereof.

In its native form, the extracellular domain of wild type TRAIL comprises residues 39 to 281 of the amino acid sequence set out in SEQ ID NO: 1. However, one or more proteolytic cleavage sites are located within the sequence between residues 39 and 114, and these cleavage sites should be excluded from the sequence providing the apoptosis-inducing activity of TRAIL.

Thus a suitable fusion protein in accordance with the invention may comprise an amino acid sequence that provides the apoptosis-inducing activity of TRAIL from which proteolytic cleavage sites have been excluded by either deletion or replacement of amino acid residues required for cleavage. Alternatively, in a suitable embodiment residues 39 to 113 may be excluded from a fragment or variant of the wild type TRAIL sequence, and the sequence in the fusion protein used as an amino acid sequence that provides the apoptosis-inducing activity of TRAIL may be based only on the amino acid sequence found at positions 114 to 281 of in SEQ ID NO: 1. In a suitable embodiment, all of these residues may be used, as found in the fusion protein the sequence of which is set out in SEQ ID NO: 3.

In the case that the amino acid sequence that provides the apoptosis-inducing activity of TRAIL comprises a variant of the extracellular domain of TRAIL, such a variant may, for example, share 90%, 95%, 96%, 97%, 98%, or 99% identity with the corresponding portion of the native TRAIL sequence (which may, for example, be the sequence at positions 114 to 281 of SEQ ID NO: 1). By the same token, a suitable variant may differ from the corresponding portion of the native TRAIL sequence (such as the sequence at positions 114 to 281 of SEQ ID NO: 1) by up to 50 amino acid residues, by up to 40 amino acid residues, by up to 30 amino acid residues, by up to 20 amino acid residues, or by up to 10 amino acid residues. A suitable derivative may differ from the corresponding portion of the native TRAIL sequence (such as the sequence at positions 114 to 281 of SEQ ID NO: 1) by 9, 8, 7, 6, 5, 4, 3, 2 or just 1 amino acid residues.

In the case that the amino acid sequence that provides the apoptosis-inducing activity of TRAIL comprises a fragment of the extracellular domain of TRAIL. It will be appreciated that fragments of this sort share 100% sequence identity with the corresponding portion of the native TRAIL sequence, but that they are truncated as compared to the native TRAIL sequence (as set out in SEQ ID NO: 1). Suitably such a fragment may, for example, consist of approximately 175, 170, or 168 contiguous amino acid residues of the native TRAIL sequence. Such a fragment may, consist of approximately 165, 160, 155, or 150 contiguous amino acid residues of the native TRAIL sequence.

"Membrane-Anchoring Amino Acid Sequence"

A "membrane-anchoring" amino acid sequence is, for the purposes of the present invention, an amino acid sequence that serves to anchor a fusion protein of the invention in the cell membrane of the cell expressing the protein. The orientation will be such that the amino acid sequence providing the apoptosis-inducing activity of TRAIL is found on the extracellular side of the membrane. This arrangement allows the fusion protein to interact with cells other than the cell in which the fusion protein has been expressed.

Merely by way of example, in a suitable embodiment the membrane-anchoring amino acid sequence may be selected from the group consisting of:

a transmembrane domain;
a glycosylphosphatidylinositol (GPI) anchor;
a sequence motif that undergoes lipid modification thereby allowing membrane anchorage of the fusion protein;
an antibody, or antigen-binding fragment thereof, the binding of which anchors the fusion protein to the membrane.

Membrane-anchoring sequences attach to the cell membrane (for example by embedding of amino acids, in the case of such sequences based on transmembrane domains, or through associated fatty acids, in the case of GPI anchors) in a manner that secures the fusion protein to the membrane.

Suitable embodiments of the membrane-anchoring domains set out above are discussed further below, however examples of membrane-anchoring sequences that go beyond those referred to above will also be known to those skilled in the art, and these too may be used in the fusion proteins of the invention.

In the case of transmembrane domains for use in the fusion proteins of the invention, a suitable domain may, for example, be from a one-pass transmembrane type1 proteins for example CD4. Alternatively, a suitable domain may be from a one-pass transmembrane type2 protein, such as CD72. A suitable domain may be from a four-pass transmembrane protein (for example CD37), and may comprise one of more of the four individual transmembrane domains found in such proteins. Alternatively, a suitable domain may be from a multiple transmembrane attachment (type III) protein, such as C5aR, and may comprise one or one of more of the individual transmembrane domains found in proteins of this sort.

In order to serve their function, membrane-anchoring sequences comprising or based upon transmembrane domains should have sufficient length to allow the sequence to become embedded in the cell membrane.

In a suitable embodiment the membrane-anchoring amino acid sequence is derived from the transmembrane domain of CD40L. For present purposes, the transmembrane domain of CD40L should be taken as consisting of the amino acid residues 13 to 44 of SEQ ID NO: 2.

In a suitable embodiment, the membrane-anchoring amino acid sequence may comprise the transmembrane domain of CD40L, or a fragment or variant thereof.

A suitable variant may be one that shares 80%, 85% 90%, 95%, 96%, 97%, 98%, or 99% identity with the corresponding portion of the native CD40L sequence (which may comprise amino acid residues 13 to 44 of SEQ ID NO: 2). By an alternative definition, a suitable variant may differ from the corresponding portion of the native CD40L sequence (which may comprise amino acid residues 13 to 44 of SEQ ID NO: 2) by up to 30 residues, by up to 20 residues, or by up to 10 residues. For instance, a suitable variant of the transmembrane domain of CD40L (comprising amino acid residues 13 to 44 of SEQ ID NO: 2) may differ from the corresponding portion of the native CD40L sequence by 9, 8, 7, 6, 5, 4, 3, 2, or 1 amino acid residues.

Fragments of the CD40L transmembrane region may be selected with reference to the considerations above regarding the lengths of sequence necessary to achieve their function.

In embodiments of the invention where the fusion proteins make use of the CD40L transmembrane region, or a fragment or derivative thereof, the region, fragment or derivative may be provided as part of a longer sequence from CD40L.

Suitable membrane-anchoring sequences that allow lipid modification of the fusion proteins of the invention may facilitate conjugation of a lipid to the fusion protein ex vivo, or may induce lipid modification in vivo. Suitable membrane-anchoring sequences for that allow lipid modification of the fusion proteins of the invention may allow expression of the fusion protein at the cell surface.

By way of example a suitable sequence allowing lipid modification may be one that promotes N-myristoylation of the fusion protein. N-myristoylation is catalyzed by N-myristoyl transferase which generally recognises the sequence Met-Gly-X-X-X-Ser/Thr at the amino terminus. Other suitable sequences allowing lipid modification may include those that promote attachment of lipids selected from the group consisting of: fatty acids, isoprenoids, sterols, phospholipids, and glycosylphosphatidyl inositol (GPI). Examples of such sequences are well known to those skilled in the art.

It will also be appreciated that fusion proteins of the invention may comprise sequences that allow modification by more than one type of lipid. Merely by way of example, fusion proteins of the invention may comprise a sequence that promotes modification by myristate and a sequence that promotes modification by palmitate; a sequence that promotes modification by palmitate and a sequence that promotes modification by cholesterol; or a sequence that promotes modification by farnesyl and a sequence that promotes modification by palmitate.

Antibodies, or antigen-binding fragments thereof, suitable for use as membrane-anchoring amino acid sequences in the fusion proteins of the invention may bind to an antigen that is a cell surface moiety (for example, a moiety selected from the group consisting of: proteins; peptides; lipids; and polysaccharides associated with the membrane). For example, a suitable fusion protein may comprise an anti-CD37 antibody, or an antigen-binding fragment thereof.

Further examples of membrane-anchoring amino acid sequences that may be used in fusion proteins of the invention include suitable integral (intrinsic) or peripheral (extrinsic) proteins that leads to expression of the fusion protein at the cell surface.

"Therapeutic Agents of the Invention"

The ability of the fusion proteins of the invention to induce apoptosis in cancer cells means that these proteins (and indirectly the polynucleotides encoding the proteins, and expression vectors comprising such polynucleotides) have therapeutic utility in the prevention and/or treatment of cancer. The inventors believe that this utility is applicable in respect of a very wide range of cancers. Further examples of such cancers that may be prevented and/or treated using the fusion proteins of the invention are described elsewhere in the specification, and include, but are not limited to: cervical cancer; pancreatic cancer; liver cancer; head or neck cancer; and breast cancer.

For the sake of brevity, fusion proteins, polynucleotides or expression vectors in accordance with any of the aspects or embodiments of the invention described herein may all be referred to as "therapeutic agents of the invention". Except for where the context requires otherwise, references to "therapeutic agents of the invention" in this manner may be considered equally applicable to any of the specific aspects or embodiments disclosed herein.

In keeping with their biological activity referred to above, and as set out elsewhere in the present specification, the invention provides medical uses of the fusion proteins, polynucleotides, and expression vectors. These medical uses may be for the prevention and/or treatment of cancer. Similarly, the invention provides methods of treatment, practiced to prevent and/or treat cancer, employing the fusion proteins, polynucleotides, or expression vectors described herein.

Specific forms of cancer in which the medical uses or methods of treatment described above may be of particular value are described further below.

In addition to the use of therapeutic agents in the treatment of cancer, it will also be appreciated that these therapeutic agents are suitable for use prophylactically in the prevention of cancer. In particular, therapeutic agents of the invention may be of prophylactic use in individuals identified as at high risk of developing cancers that are TRAIL Receptor (DR4 or DR5 or both) positive.

"A Therapeutically Effective Amount"

A "therapeutically amount" of a therapeutic agent of the invention is an amount of such an agent that is, whether provided in a single dose or cumulatively over time, sufficient to induce a degree of cancer cell apoptosis that provides a therapeutic benefit. By way of example, a therapeutically effective amount of a therapeutic agent of the invention may be one able to meet one or more of the following criteria: capable of effecting a reduction in tumour size; capable of slowing tumour growth.

While it will be appreciated that it is the fusion proteins of the invention that exert the ability to induce cancer cell apoptosis, the concept of a therapeutically effective amount in the context of the present disclosure applies not only to such proteins, but also to polynucleotides or expression vectors of the invention. While a therapeutically effective amount of a fusion protein of the invention is capable of "directly" inducing the requisite cancer cell apoptosis, the polynucleotides of the invention induce such apoptosis "indirectly"—by giving rise to expression of the biologically active fusion protein. Thus, in the contexts of polynucleotides or expression vectors of the invention, therapeutically effective amounts are amounts that are sufficient to bring about the expression of a therapeutically effective amount of the fusion protein of the invention.

DETAILED DESCRIPTION OF THE INVENTION

As described elsewhere in the present specification, the fusion proteins of the invention, in which sequences providing the apoptosis-inducing activity of TRAIL are secured to the cell membrane by an anchoring sequence, have improved cancer cell-killing activity as compared to naturally occurring TRAIL. In a suitable embodiment the amino acid sequence that provides the apoptosis-inducing activity of TRAIL may be selected so that it does not contain a protease cleavage site. Suitably such a sequence may, for example, be a fragment chosen for the absence of a cleavage site, or a derivative in which a cleavage site has been disrupted.

Additionally or alternatively, a fusion protein of the invention may comprise a membrane-anchoring amino acid sequence selected so that it does not contain a protease cleavage site. As with the preceding paragraph such a sequence may, for example, be a fragment chosen for the absence of a cleavage site, or a derivative in which a cleavage site has been disrupted. The fragment of the CD40L transmembrane domain utilised in the specific fusion protein of SEQ ID NO: 3 represents an example of a membrane-anchoring sequence that has been chosen in this manner, since it ends before the cleavage site found at amino acid residues 110-116 of wild-type CD40L. It will be appreciated that omission of the cleavage site in this manner facilitates retention of the fusion protein on the cell surface. This chosen fragment of the CD40L transmembrane domain, or derivatives of this fragment, represents a preferred membrane-anchoring sequence for use in the fusion proteins of the present invention. Similarly, other fragments of the CD40L transmembrane region from which the naturally occurring cleavage site at residues 110 to 116 has been omitted, or derivatives of such fragments, constitute further preferred examples of membrane-anchoring amino acid sequences suitable for use in the fusion proteins of the invention.

As has been referred to above, the therapeutic agents of the invention are suitable for use as medicaments for the prevention and/or treatment of cancer. In particular, the therapeutic agents of the invention are suitable for use as medicaments in the prevention and/or treatment of cancer that comprises cells expressing TRAIL-R1 (also referred to as DR4) and/or TRAIL-R2 (also referred to as DR5).

The determination of whether or not a cancer comprises cells that express TRAIL-R1 or TRAIL-R2 is a simple manner, and the skilled person will be able to identify many suitable assays by which the presence or absence of TRAIL-R1 and/or TRAIL-R2. Merely by way of example, immunolabelling of biopsy samples (such as histological samples) may be undertaken, for example using suitable commercially available antibodies. Examples of such antibodies include an antibody to TRAIL-R1 with the catalogue number "ab16955" and an antibody to TRAILR-2 with the catalogue number "ab16942", both of which are available from Millipore). Alternatively, a suitable approach may involve investigation of gene expression in a population of cells including the cancer cells of interest, for example by RT-PCR or other techniques known to those skilled in the art.

While assaying cancers for the presence of cells expressing TRAIL-R1 and/or TRAIL-R2 is not currently standard clinical procedure, this may be readily adopted once the benefits provided by the present invention have been appreciated.

In view of the above, it will be appreciated that subjects with cancer comprising cells positive for TRAIL-R1 and/or TRAILR-2 represent a preferred subgroup of patients that may derive benefit from the prevention and/or treatment of cancer through the medical use of therapeutic agents of the invention.

The invention also provides a method of determining suitability of a subject for treatment using the fusion proteins of the invention (for example in the methods of the invention), the method comprising assaying a sample comprising cells from the subject for the expression of TRAIL-R1 and/or TRAIL-R2, wherein the presence of TRAIL-R1 and/or TRAIL-R2 expression indicates that the subject may benefit from treatment using the fusion proteins of the invention methods of the invention, and wherein an absence of TRAIL-R1 and/or TRAIL-R2 expression indicates that the subject will not benefit from treatment using the fusion proteins of the invention. Treatment using the fusion proteins of the invention may be achieved by provision of a nucleic acid encoding the fusion protein. Suitably, the method of determining suitability referred to above may further comprise a step of providing treatment using the fusion proteins of the invention (for example in the methods of treatment of the invention) when it is indicated that a subject will benefit from such treatment.

Polynucleotides encoding the fusion proteins of the invention represent a second aspect of the invention, and an example of such a polynucleotide is provided by SEQ ID NO:4 below.

As referred to above, expression vectors that comprising a polynucleotide encoding a fusion protein of the invention are themselves a third aspect of the present invention. Suitably, the vector may comprise a conditionally replicating virus.

DNA delivery systems, such as, but not limited to, the vectors of the invention, are suitable for use as therapeutic agents of the invention. The skilled person will be aware of a wide range of DNA delivery systems that may be employed for such use, and these DNA delivery systems, whether vectors or otherwise, may be used in the medical uses of the invention, incorporated in pharmaceutical compositions of the invention, and/or used in methods of treatment of the invention As demonstrated further in the Examples below, the fusion proteins of the invention have been shown to be effective in inducing death of cancer cells derived from a range of different carcinomas types. Accordingly, the inventors believe that the therapeutic agents of the invention may be of use in the prevention and/or treatment of cancers including, but not limited to, the group consisting of: cervical cancer; pancreatic cancer; liver cancer; head or neck cancer; and breast cancer.

The skilled person will appreciate that there are many suitable routes of administration by which pharmaceutical compositions of the invention or expression vectors of the invention may be provided to a subject.

The invention will now be further defined with reference to the following Examples, and the accompanying Figures, in which:

FIG. 1 illustrates PCR amplification of the CD40L N-terminal (1-324 bp) and TRAIL C-terminal domain (340-846 bp). 5 μl of the purified PCR products were run in 1% agarose gel containing 0.2 μg/ml ethidium bromide. The amplified fragment runs at an expected size. Lane M is the DNA ladder, lane 1 is the amplified CD40L fragment, and lane 2 is the amplified TRAIL fragment;

FIG. 2 shows agarose gel electrophoresis of the PCR amplified CD40LTRAIL fusion protein of the invention. 5 μl of the purified PCR product was run in 1% agarose gel containing 0.2 μg/ml ethidium bromide. The amplified fragment runs at the expected size of 831 bp;

FIG. 3 illustrates analysis of the pShuttle-CMVCD40LTRAIL minipreped DNA. Empty pShuttle-CMV or pShuttle-CMVCD40LTRAIL were digested with SalI and HindIII for one hour and analysed using 1% agarose gel electrophoresis. Lane M is a DNA ladder, lane 1 is the empty vector, lane 2 is pShuttle-CMVncCD40LTRAIL;

FIG. 4 sets out analysis of PAdshuttle-CMV-CD40LTRAIL recombinants. Kanamycin-positive selected clones were digested with PacI restriction endonuclease and the restriction products were analysed using 1% agarose gel electrophoresis. Lane M is DNA ladder; lane 1 is empty pAdeasy-1 vector; lanes 2, 7 and 8 show the correct orientation of recombinant PAdshuttle-CMV-CD40L-TRAIL clones; lanes 3, 4 and 5 refer to pShuttle-CMV CD40LTRAIL; lane 6 refers to the recombinant PAdshuttle-CMV-CD40L-TRAIL but with the wrong orientation;

FIG. 5 illustrates Confirmation of the retention of CD40L-TRAIL protein fusion expressed by RAdCD40LTRAIL at the cell surface. Panel A: EJ cells were infected with 50 MOI of either RAdTRAILwt (AdL) or RAdCD40LTRAIL (AdnL) or RAdMock (AdM) or left uninfected as a negative control. Samples were collected from the culture media 24 and 48 hours post-infection for sTRAIL measurement utilising a sTRAIL ELISA assay kit (R&D Biosystems MAB3751). Panel B: EJ cells infected with 50 MOI of RAdTRAILwt (AdL) or RAdCD40L-TRAIL (AdncL) RAdMock (AdM) or left uninfected as a negative control were grown for 48 h, cells were lysed in situ and 60 μg of total protein lysates were examined for TRAIL expression using specific antibody raised against TRAIL C-terminus domain. β-actin was also examined as a loading control;

FIG. 6 illustrates the effect of RAdCD40LTRAIL compared to RAdTRAILwt on carcinoma cell viability. Panel A: The above indicated carcinoma cell lines (EJ, Hela, Panc1, HepG2) were either infected with of RAdMock (AdM), RAdTRAILwt (AdwL) or RAdCD40LTRAIL (AdncL) at the indicated MOI or left untreated as a negative control and seeded at a density of 6000 cells/100 μl/well in 96 well microplate for 48 hours. Cell viability was then assessed using the WST-1 assay reagent. Results are an average of triplet samples±SD. Panel B: Pancreatic cell line Panc1 was either infected at 100 MOI with RAdMock, RAdTRAILwt or RAdCD40LTRAIL or left uninfected or treated with recombinant soluble TRAIL at 100 ng/ml (sTRAIL) were treated with or without the pan-caspase inhibitor zVAD at a concentration of 30 μM and seeded at a density of 6000 cells/100 μl/well in 96 well microplate for 36 hours. Caspase 3/7 activity was then assessed utilizing the Caspase-Glo 3/7 Assay reagent according to the manufacturer's instructions (Promega, cat G8091). Results represents mean of triplet samples±SD;

FIG. 7 shows the results of FACS analysis of TRAILR1 and TRAILR2 expression in head and neck carcinoma cell lines BHY (a human oral SCC cell line); PE/CA PJ15 (a human oral SCC cell line of the tongue); and Hn (a human SCC cell line of the soft palate). FACS analysis was undertaken using: Anti-Human CD261 (also known as: TRAIL Receptor 1, TRAIL-R1, TRAILR1, DR4) PE, Clone: DJR1, Cat No: 12-6644-41; Anti-Human CD262 (also known as: Trail-R2, DR5) PE, Clone: DJR2-4 (a.k.a. 7-8), Cat. No: 12-9908-41; and Isotype: Mouse IgG1 K Isotype Control PE, Clone: P3.6.2.8.1, Cat No: 12-4714-42. All antibodies were purchased from ebioscience;

FIG. 8 shows the effect of the membrane bound CD40L TRAIL fusion protein (AdncL) versus the wild-type TRAIL and recombinant soluble TRAIL (rsTRAIL) on cell viability. The human squamous cell carcinoma (SCC) cell lines BHY, HN and PE-CA-PJ15 were infected with 100 MOI of either RAdMock (AdM), RAdwtTRAIL (Adwt) or AdncCD40LTRAIL (AdncL) or treated with rsTRAIL at a concentration of 100 ng/ml or left untreated as a negative control for 48 hours. Cell viability was then assessed with WST-1 assay (Roche cat no 05015944001). Results represent a mean of triplet samples+/−SD;

FIG. 9 illustrates inhibition of TRAIL binding to TRAIL receptors in RAdCD40LTRAIL-infected cells by neutralizing the expressed CD40LTRAIL via TRAIL monoclonal antibody or competing the binding by recombinant soluble TRAIL (rsTRAIL) restores cell viability. The pancreatic cell line Panc1 cells were infected with either RAdMock (AdM) or RAdTRAILwt (AdL) or RAdCD40LTRAIL (AdncL) at 100 MOI or left untreated as a negative control or treated with rsTRAIL at a concentration of 100 ng/ml, RAdCD40LTRAIL-infected cells were treated with an increasing concentrations (0.5, 1, 2 and 4 μg/ml) of the neutralising mouse monoclonal TRAIL antibody (ab2219, 2E5), or at a fixed concentration (2 μg/ml) of the monoclonal isotype mouse IgG1 control as a negative control, or treated with an increasing concentrations (50, 100 and 200 ng/ml) of rsTRAIL or left untreated as a negative control. Cells were seeded at a density of 6000 cells/100 μl/well in 96 well microplate for 36 h. (A) cell viability were examined by WST-1 assay reagent. Results are a mean of three triplicate samples±SD, (B) microscopic pictures were taken for each treatment highlighting the visual effect of each treatment on the cells;

FIG. 11 shows sequence alignment between Fas ligand, CD40L, and TRAIL;

Figure 12:
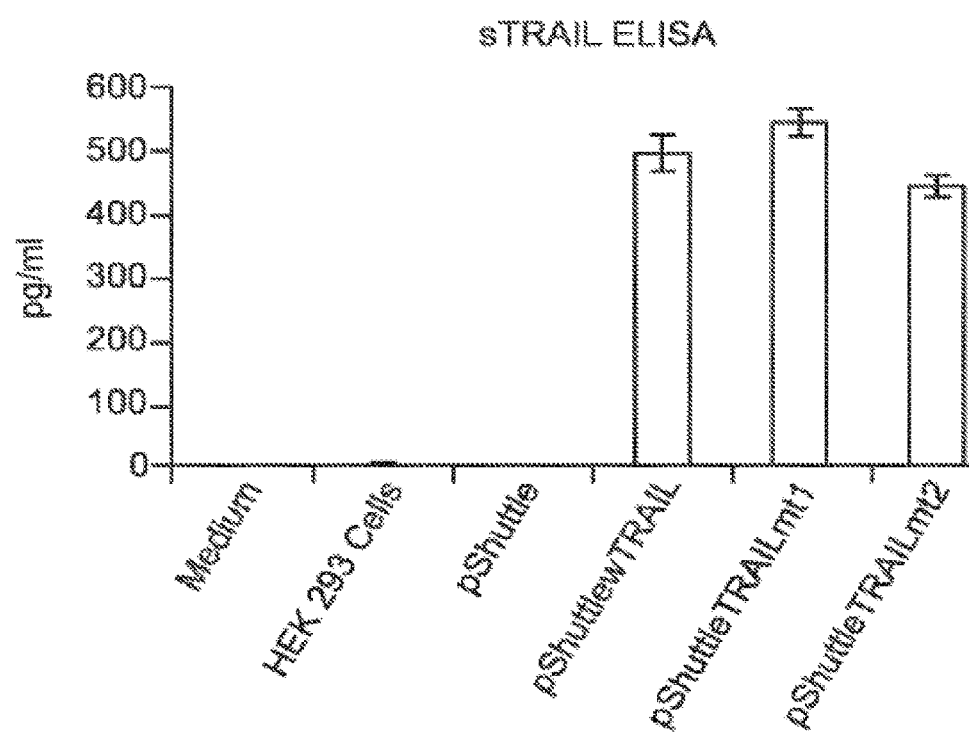
Figure 13:
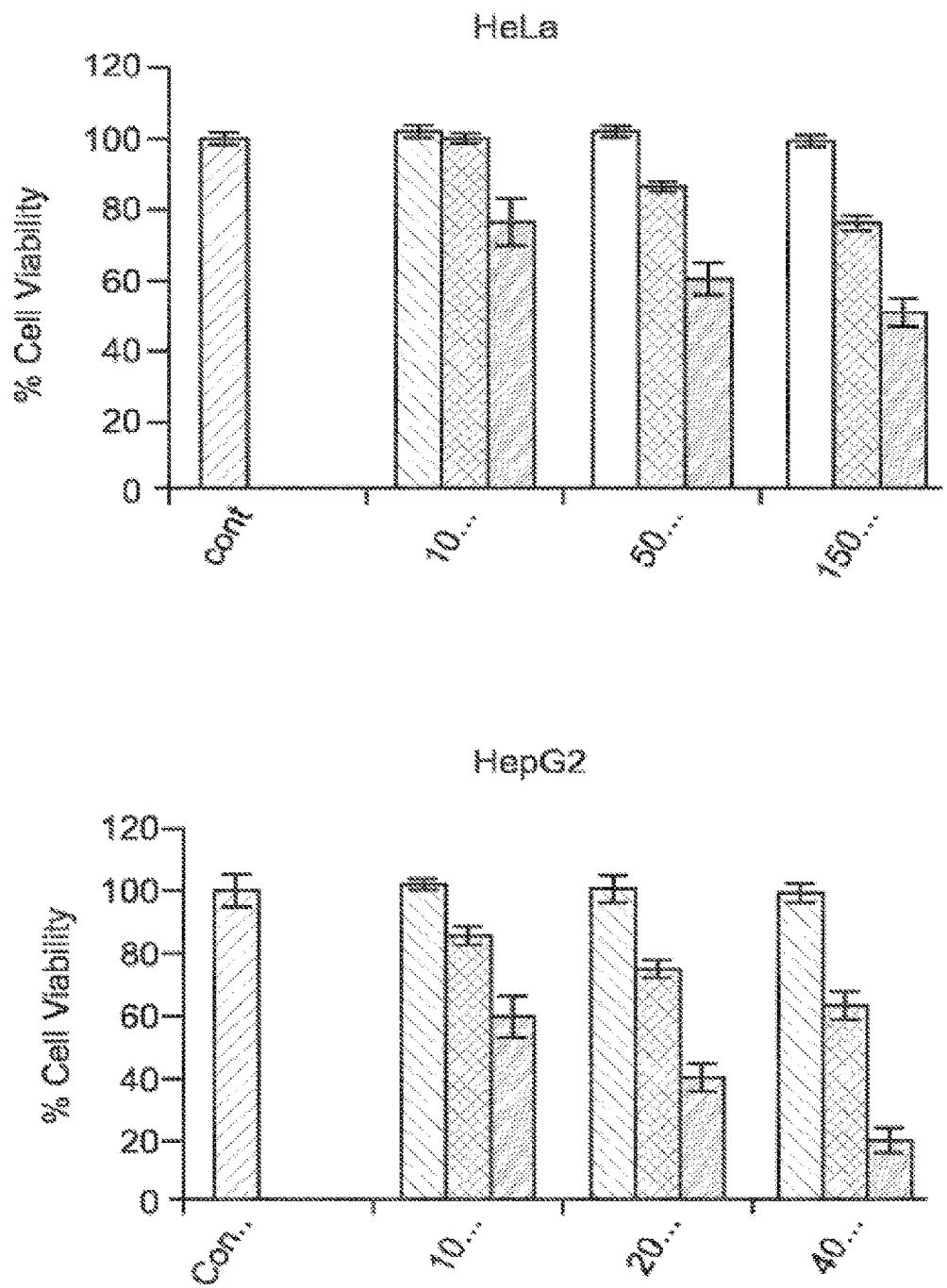

FIG. 12 shows the results of ELISA for TRAIL in media conditioned by a range of cells: HEK 293 cells transfected with 1 μg DNA of pShuttle wt TRAIL, pShuttle TRAILmt1, pShuttle TRAILmt2, pShuttle CMV, or left untransfected as a negative control. Samples were collected from the culture media 48 hours after transfection and assessed for the present of sTRAIL; and FIG. 13 illustrates the sensitivity of HeLa and HepG2 cells to fusion proteins of the invention (as exemplified by SEQ ID NO:3).

EXAMPLES

1. Generation of Polynucleotides, Expression Vectors, and Fusion Proteins in Accordance with the Invention 1.1 Generation of CD40L N-Terminal Fragment (1-324 bp)

A pCLneoCD40L construct together with a couple of forward CD40L1Sal1F (AGTC GAC ATG ATC GAA ACA TAC AAC CA) (SEQ ID NO: 10) and reverse primers CD40L$_{324R}$ (TTC TTT CTT CGT CTC CTC TTT GTT) (SEQ ID NO: 11), were used under the following the PCR condition (93° C. 5 mins (93° C. 30 Sec, 58.1° C., 45 Sec, 72° C. 2 mins)×25, 72° C., 5 mins).

1.2 Generation of TRAIL C-Terminus Region (340-846 bp)

A pcDNATRAIL construct together with a couple of forward CD40L$_{324}$TRAIL$_{340}$F (Tataatgttaaacaaagaggagac-gaagaaagaa GTG AGA GAA AGA GGT CCT CAG AGA GTA) (SEQ ID NO: 12) and reverse primer TRAIL$_{846}$ HindIIIR (A AA GCT TTT AGC CAA CTA AAA AGG CC) (SEQ ID NO: 13) were used to generate a TRAIL region (340-846 bp) fused to a CD40L oligonucleotide spanning 291-324 bp under the following PCR reaction conditions 93° C. 5 mins (93° C. 30 Sec, 58.4° C., 45 Sec, 72° C. 2 mins)×25, 72° C., 5 mins.

1.3 Generation of the Final CD40L-TRAIL Fusion

Figure 1:
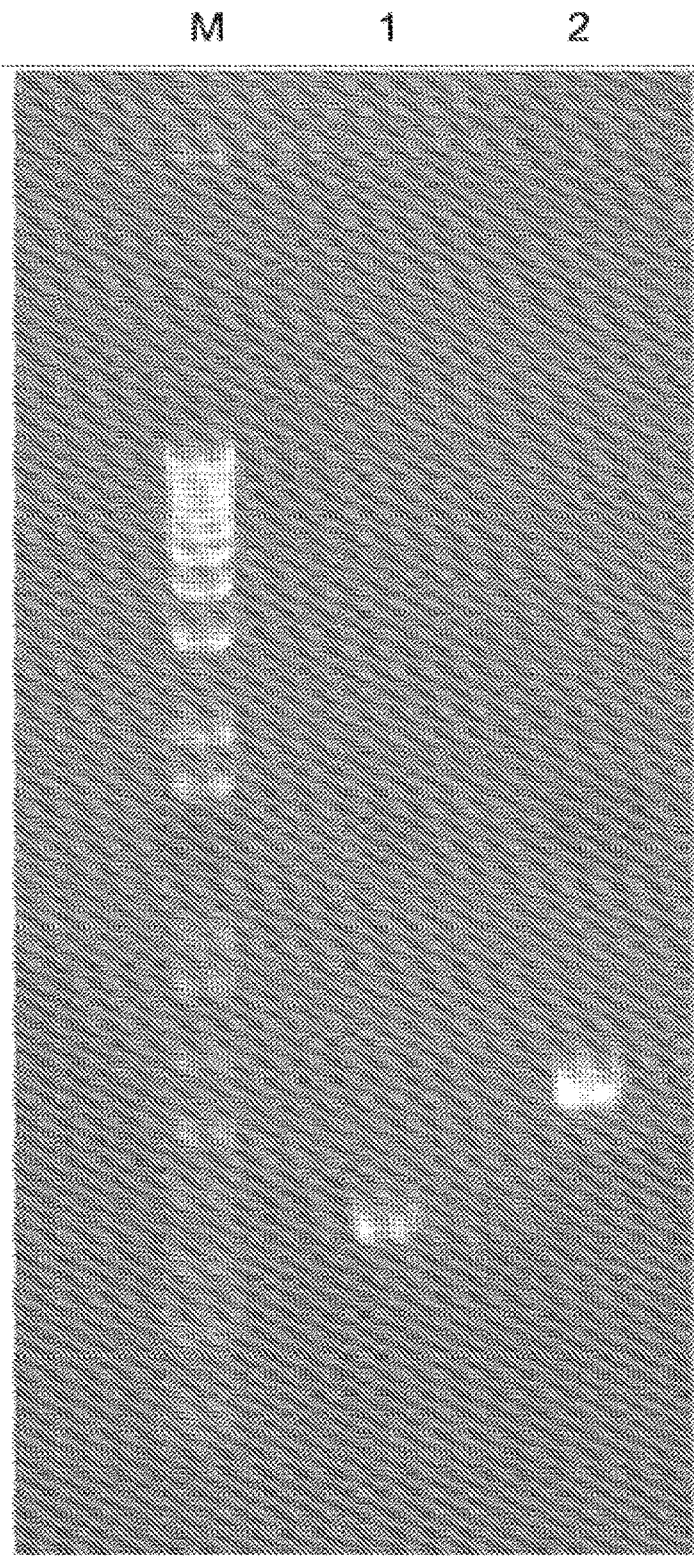
Figure 2:
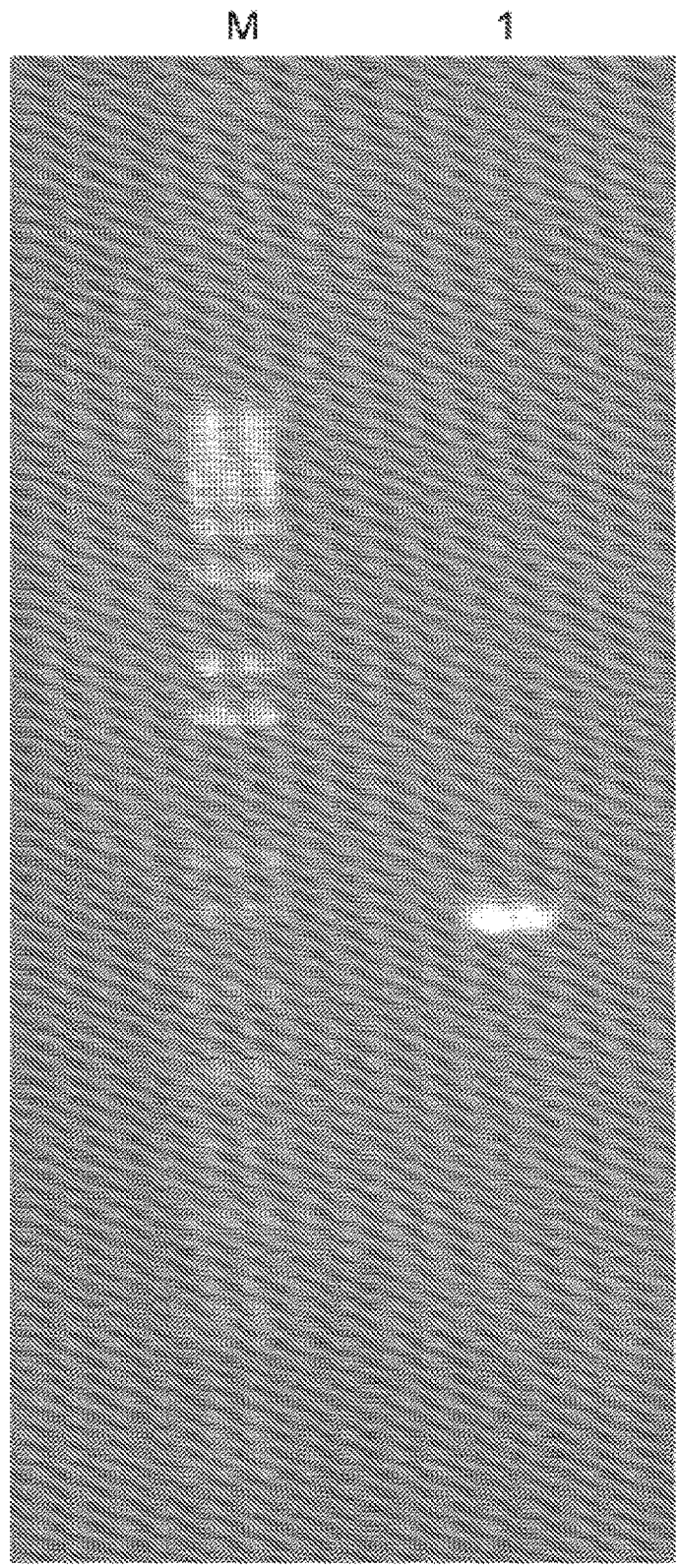

To generate the CD40L (1-324 bp) and TRAIL fragment (340-846 bp), 100 pg of CD40L PCR DNA fragment was equally mixed with TRAIL PCR DNA fragment. The CD40LTRAIL fusion fragment was then amplified by PCR using the forward primer CD40L1Sal1F (AGTC GAC ATG ATC GAA ACA TAC AAC CA) (SEQ ID NO: 10) and the reverse primer TRAIL$_{846}$ HindIIIR (A AA GCT TTT AGC CAA CTA AAA AGG CC) (SEQ ID NO: 13), the amplified fragment was then gel purified and analyzed by 1% agarose gel electrophoresis technique as shown in FIG. 2.

1.4 Cloning the CD40L-TRAIL DNA Fusion into the pShuttle CMV Vector.

The CD40L-TRAIL DNA fusion amplified fragment was gel purified and cloned into Topo2.1 plasmid, minipreped DNA was then digested with SaII and HindIII enzymes to release the CD40LTRAIL fusion, the purified CD40LTRAIL DNA fragment was then ligated into SaII/HindIII predigested and purified pShuttle-CMV vector, the sequence of CD40L-TRAIL fusion was then confirmed by sequence analysis and restriction digestions.

1.5 Generation of Recombinant Adenoviral Plasmids by Homologous Recombination in *E. coli*

Once we confirmed the cloning of CD40L-TRAIL DNA fusion in frame with the CMV promoter in pShuttle-CMV vector, we used the AdEasy system (Quantum Biotechnology) using adenovirus vector and method as published by Chuan He and co-workers (He, Zhou et al. 1998).

The pAdEasy-1 adenoviral plasmid contains all Ad5 sequences except nucleotides 1-3,533 (encompassing the E1 genes) and nucleotides 28,130-30,820 (encompassing E3). The left arm of the pShuttle CMV vector contains the Ad5 nucleotides 34,931-35,935. The right arm contains Ad5 nucleotides 3,534-5,790 which mediate homologous recombination with the PAdEasy-1 vector in *E. coli*, plus inverted terminal repeat (ITR) and packaging signal sequences (nucleotides 1-480 of Ad5) required for viral production in mammalian cells. To insert the CD40L-TRAIL DNA fusion sequence into the Adenoviral backbone, the pShuttle CD40LTRAIL construct was homologously recombined with PAdEasy-1 vector.

Typically, 1.0 μg of pShuttle-CMVCD40LTRAIL vector was linearized with PmeI, purified by phenol/chloroform extraction, and mixed with 0.1 μg of pAdEasy-1 in a total volume of 6 μl. The DNA mixture was used to transform 20 μl of electrocompetent *E. coli* BJ5183 cells by electroporation method. The cell suspension was then plated onto LB-agar medium containing 50 μg/ml kanamycin and incubated at 37° C. until colonies showed up. The smaller colonies (which usually represented the recombinants) were picked up and grown in 2 ml of L-Broth containing 50 μg/ml of kanamycin. Clones were first screened by analyzing their supercoiled sizes on agarose gels, comparing them to pAdEasy-1 control. Those clones that had inserts were further examined by Pac1 restriction endonuclease digestion. Once confirmed, supercoiled plasmid DNA was transformed into Topo 10F chemically competent cells for large-scale DNA amplification.

2. Cellular Expression of Fusion Proteins
Production of Adenoviruses in Mammalian Cells Approximately $1.5 \times 10^6$ of 911 or HEK 293 cells were plated in 25 cm$^2$ flasks 24 hr before transfection, by which time they reached 50-70% confluency. Cells were washed once with 3 ml of OptiMEM, then 2.5 ml of OptiMEM was added to each flask and the flasks returned to the CO2 incubator for 30 mins before transfection. 4 μg of recombinant adenoviral vector DNA, digested with PacI and phenol/chloroform purified and 20 μl of Lipofectamine were added to 500 μl of OptiMEM according to the manufacturer's instructions. After incubation at room temperature for 30 min, the transfection mix was added to the cells in the 25 cm$^2$ flasks. After 6 hours at 37° C., the medium containing the transfection mix was removed, and 6 ml of growth medium with (30 μM of the general caspase inhibitor zVAD) was added to inhibit possible cell death by CD40LTRAIL protein expression as HEK293 cells are TRAILR1 and 2 positive. Transfected cells were monitored and collected 7-10 days after transfection by scraping cells off flask and pelleting them along with any floating cells in the culture. The supernatant was discarded and the cell pellet were re-suspended in 2 ml sterile PBS and viral particles were extracted by vigorous mixing with an equal volume of Arklone P and spinning for 10 min at 2000 rpm. The viral containing solution was collected and stored at −70° C. or used to infect $3-5 \times 10^6$ 293 cells in a 25 cm$^2$ flask. Four days later, viruses were harvested.

For large-scale recombinant adenoviral production, HEK 293 cells were plated out into twelve 150 cm$^2$ flasks (IWAKI). At 80% confluency, the complete growth medium was removed and cells were supplemented with 5 ml 2% FCS D-MEM with 1:100 dilution of the adenoviral extract solution. After 6 hours cells were supplemented with an additional 15 ml of 2% FCS D-MEM medium (30 μM of the general caspase inhibitor zVAD) and allowed to incubate at 37° C. 5-6 days post-infection, cells and medium were transferred to a 50 ml tube and centrifuged at 2000 rpm for 5 minutes at room temperature. The supernatant was discarded and the cell pellets were re-suspended in 10 ml sterile PBS and viral particles were extracted by Arklone P.

3. Expression of Fusion Proteins at the Cell Surface

To test whether CD40LTRAIL protein delivered by RAdCD40LTRAIL vector resists the cleavage from cell surface, bladder carcinoma cells were either infected with 100 MOI of RAdMock, RAdTRAILwt (expressing wild-type TRAIL: 1-846 bp) or RAd CD40LTRAIL or left uninfected as a negative control for 48 h. Cell-free media were collected from each setting at 24 and 48 h for sTRAIL assessment utilizing the sTRAIL ELISA assay kit (R&D Biosystems MAB3751). Cells were also lysed in situ for western blot analysis.

Figure 5A:
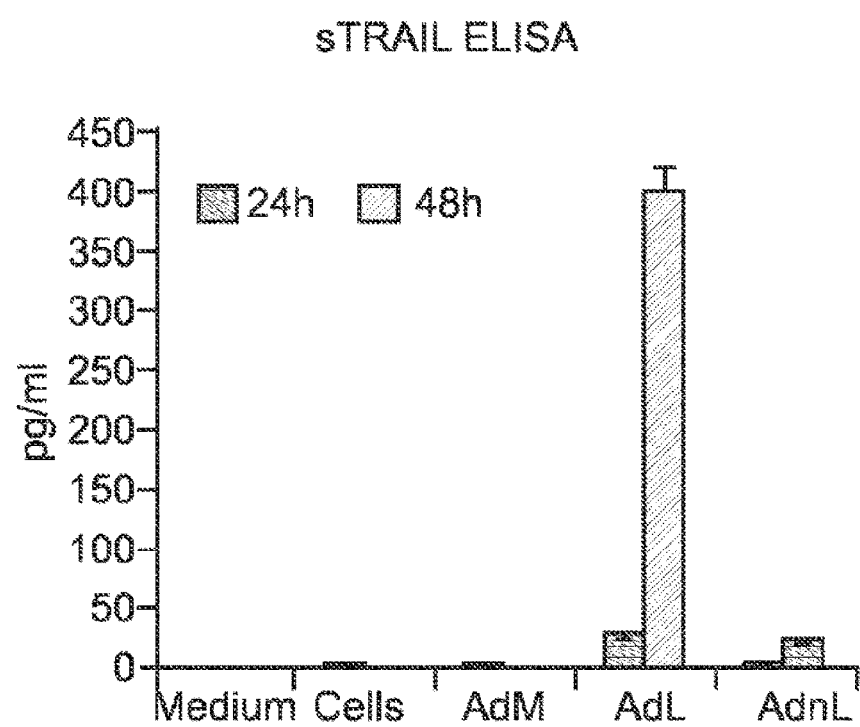

As shown in FIG. 5A, sTRAIL was detected in RAdTRAILwt-infected cells in a time dependent manner (at 48 hs≥380 pg/ml), whereas less than 30 pg/ml of sTRAIL were detected in cell-free medium obtained from RAdCD40LTRAIL-infected cells which could be attributed to TRAIL leaked from dead cells. Taken together these results indicate that the generated CD40L-TRAIL fusion protein is resistant to cleavage from membrane.

Figure 5B:
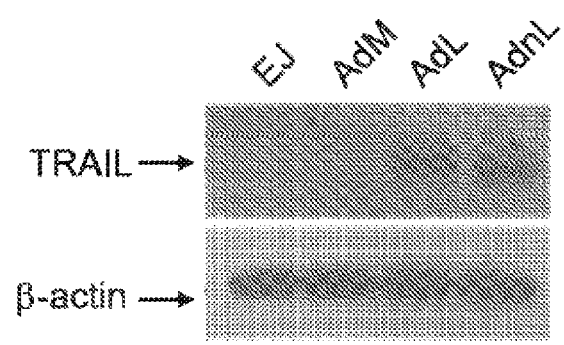

Wild-type TRAIL and CD40L-TRAIL were expressed from RAdTRAILwt and RAdCD40LTRAIL-infected cells respectively as determined by western blot analysis of total cell lysates (FIG. 5B), using TRAIL specific antibody (Santa Cruz biotechnology Sc-1889) raised against the TRAIL c-terminus. CD40LTRAIL fusion runs slightly at a lower molecular weight compared to TRAIL wild-type protein as expected.

Figure 3:
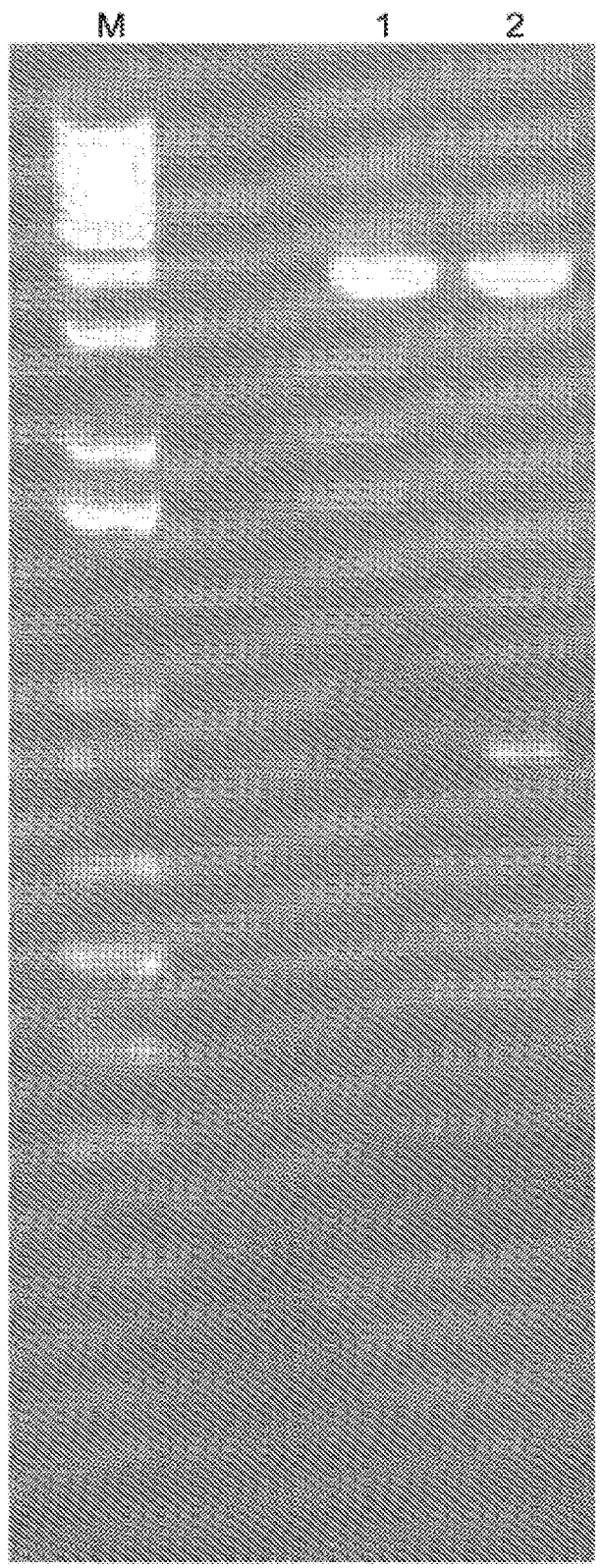
Figure 4:
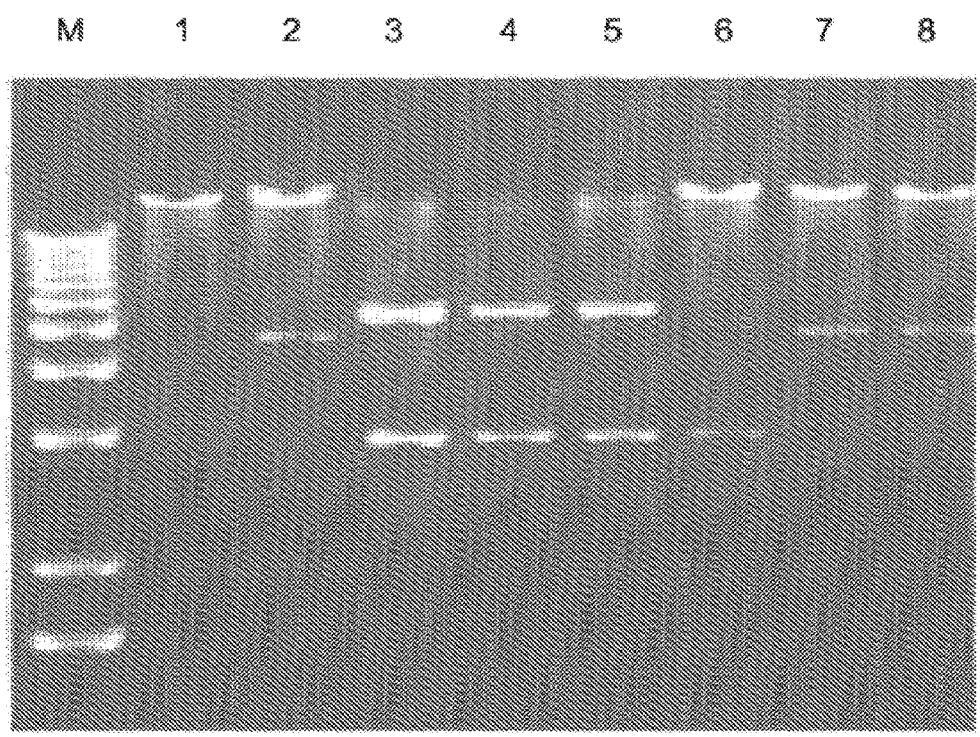
Figure 6A:
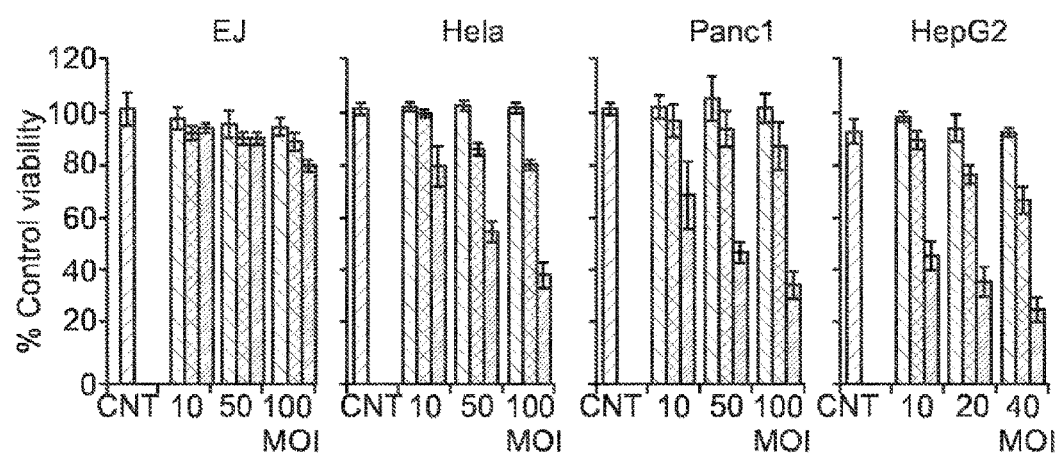
Figure 6B:
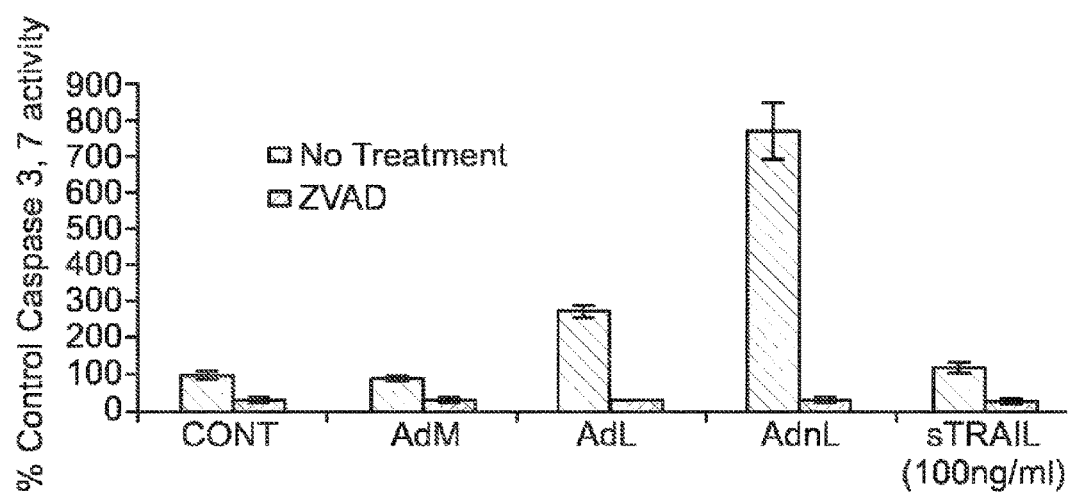

4. Fusion Proteins of the Invention Reduce Viability and Induce Apoptosis in Cancer Cell Lines Expressing TRAIL Receptors To examine the direct effect of the generated CD40L-TRAIL adenovirus compared to RAdTRAILwt, several carcinoma cell lines including the bladder carcinoma EJ, the cervical carcinoma Hela, the pancreatic carcinoma Panc1 and the liver HepG2 were either infected with of RAdMock, RAdTRAILwt or RAdCD40LTRAIL at the indicated MOI as shown in FIG. 3, or left untreated as a negative control and seeded at a density of 6000 cells/100 µl/well in 96 well microplate for 48 hours. Cell viability was then assessed by WST-1 assay reagent. As shown in FIG. 6A, Hela, Panc1 and HepG2 cells exhibit varying degrees of sensitivity toward the CD40L-TRAIL fusion protein and to a lesser extent to AdTRAILwt, however no cell viability reduction was observed in EJ where expression of TRAIL Receptor 1 and 2 is very low (data not shown). To examine whether this cell viability reduction is attributed to caspase activation and subsequent apoptosis induction, caspases 3,7 activity was assessed in Panc1 cells. As shown in FIG. 6B, higher caspase 3,7 activity was observed in RAdCD40LTRAIL-infected cells compared to RAdTRAIL wt control cells.

Figure 7:
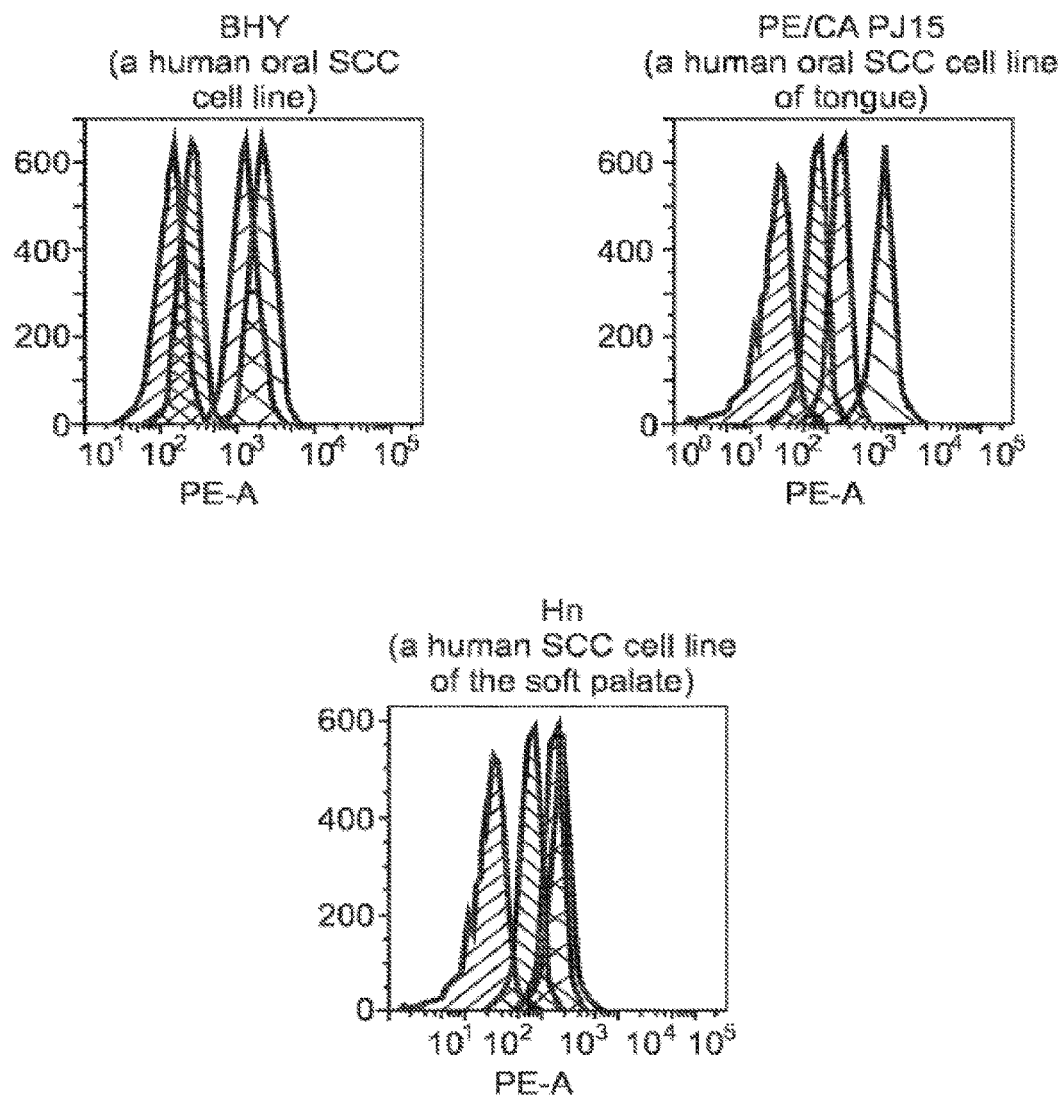
Figure 8:
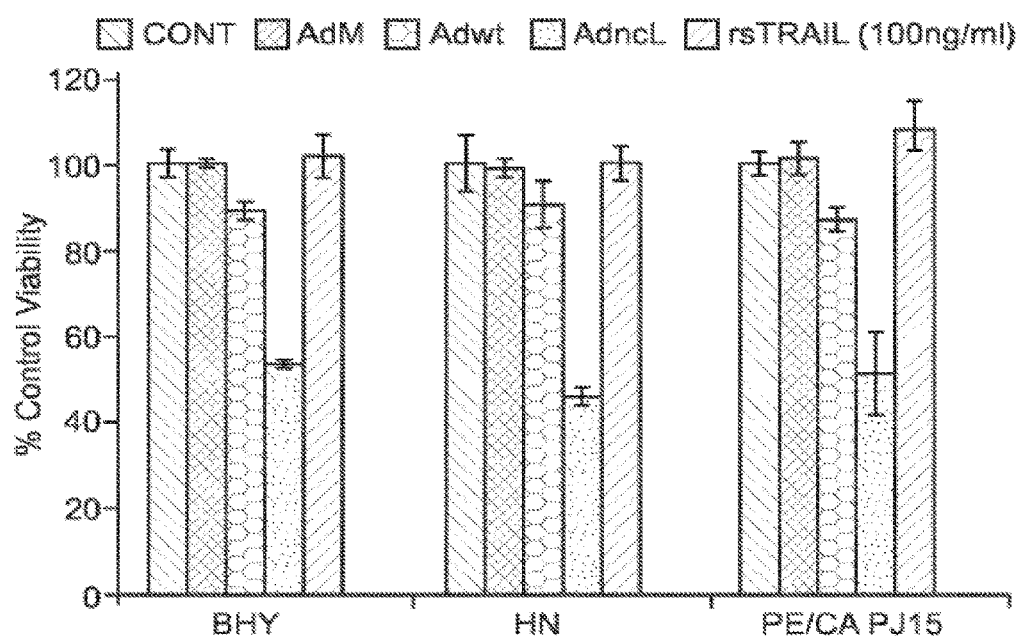

This was further illustrated in a study using head and neck cancer cell lines, the results of which are set out in FIGS. 7 and 8. These results show that human squamous cell carcinoma (SCC) cell lines expressed the TRAIL receptors TRAILR1 and TRAILR2, and that transfection of these cell lines with expression vectors encoding the fusion protein of the invention set out in SEQ ID NO:3 significantly reduced viability of these cells.

Figure 9:
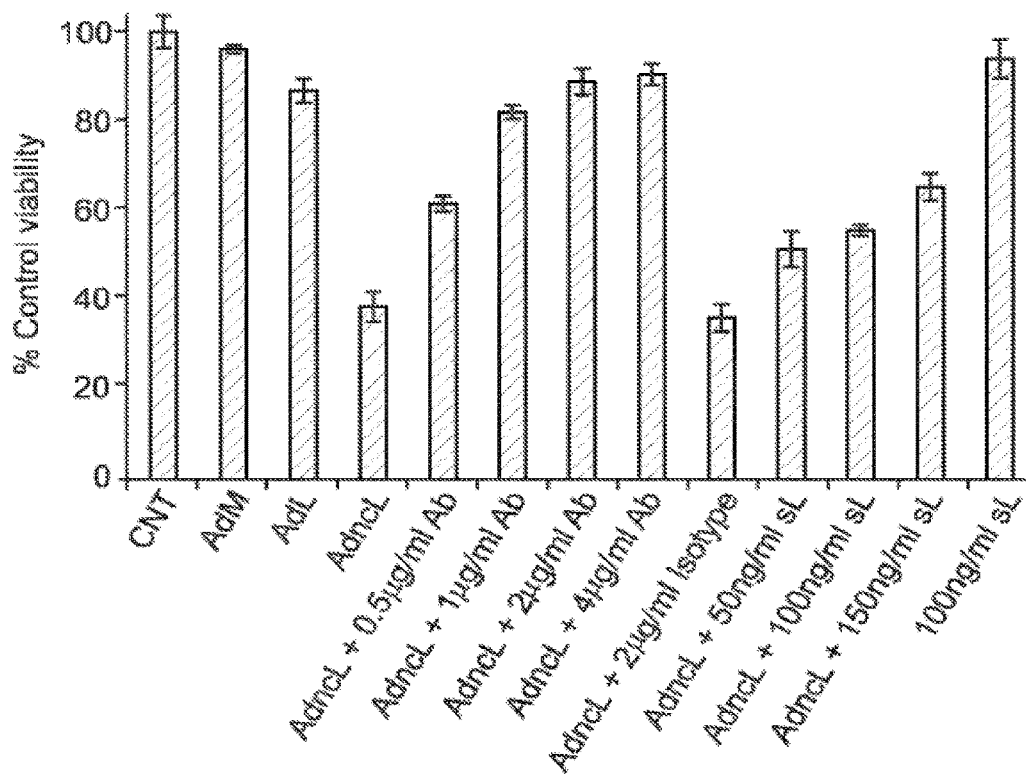

5. Inhibition of Binding of Fusion Proteins of the Invention to TRAIL Receptors Restores Cancer Cell Viability It was important to confirm that the observed cell viability reduction is specifically due to CD40L-TRAIL expression. Therefore, we examined the effect of the neutralizing monoclonal antibody (ab2219, 2E5) on RAdCD40LTRAIL-induced cell viability reduction. Pancreatic carcinoma cells, Panc1, were infected with either RAdMock or RAdTRAILwt or RAdCD40LTRAIL at 100 MOI or left untreated as a negative control or treated with rsTRAIL at a concentration of 100 ng/ml. Cells were then treated with increasing concentrations (0.5, 1, 2 and 4 µg/ml) of the neutralising mouse monoclonal TRAIL antibody (ab2219, 2E5), or at a fixed concentration (2 µg/ml) of the monoclonal isotype mouse IgG1 as a negative control, or treated with increasing concentrations (50, 100 and 200 ng/ml) of rsTRAIL or left untreated as a negative control. Cells were then seeded at a density of 6000 cells/100 µl/well in 96 well microplate for 36 h. Cell viability was then assessed by WST-1 assay reagent. As shown in FIG. 9, RAdCD40LTRAIL-infected Panc1 cells exhibited reduced cell viability. However, neutralizing the expressed CD40LTRAIL by the 2E5 neutralizing antibody significantly restored cell viability in a concentration-dependent way. This was caused by blocking CD40L-TRAIL binding to TRAIL receptors via antibody binding to the CD40LTRAIL, since the isotype control antibody was unable to restore cell viability. Furthermore, addition of soluble TRAIL into RAdCD40LTRAIL-infected cells resulted in partial restoration of cell viability, which could be attributed to the competition between soluble and membrane bound TRAIL on binding to the active TRAIL receptors. This result clearly shows the inhibitory effect of the CD40LTRAIL on TRAIL receptor-positive carcinoma cells.

Figure 10:
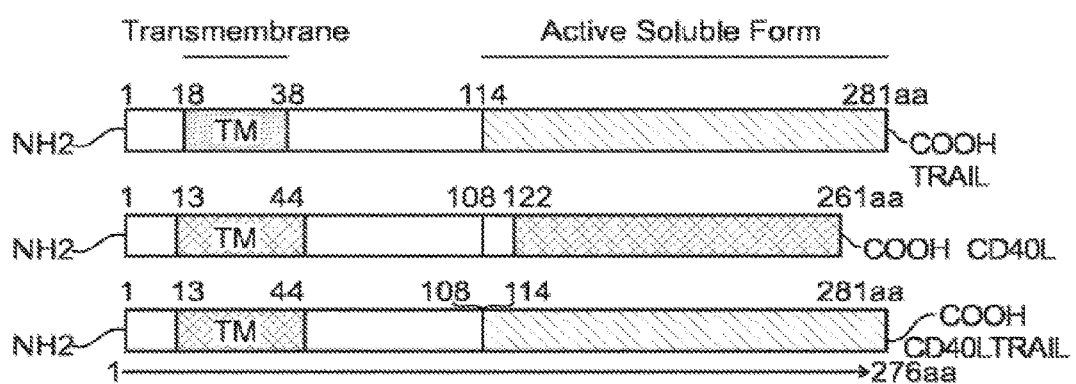
FIG. 10 is a schematic representation of TRAIL, CD40L, and the CD40L/TRAIL fusion protein of SEQ ID NO:3.

6. Data to Illustrate that the Strategy to Mutate the Cleavage Point of TRAIL Did not Work The structures of TRAIL, CD40L and CD40LTRAIL fusion referred to below are shown schematically in FIG. 10.

6.1 Generation of TRAIL Mutant Resistant to MMP Cleavage

Previous work from our laboratory has shown that FasL lacking the $^{128}$EKQI$^{131}$ (SEQ ID NO: 14) cleavage site is retained at the cell membrane and is more potent in inducing apoptosis than the wild-type protein. Furthermore, we also identified a CD40L cleavage site $^{110}$SFEMQKG$^{116}$ (SEQ ID NO: 15) by sequence alignment between FasL and CD40L (Elmetwali et al., 2010, Knox et al., 2003, Milner et al., 2002). Therefore, we sought to identify a possible TRAIL cleavage site and attempted to acquire information through sequence alignment between the published FasL and CD40L cleavage sites and TRAIL. This sequence alignment led us to an 105EKQQ$^{108}$ (SEQ ID NO: 16) site in TRAIL (FIG. 11), which was similar to the FasL cleavage site $^{128}$EKQI$^{131}$ (SEQ ID NO: 14), and, on this basis, we generated TRAIL mutants lacking the amino acid sequence from 105-108 and from 105 to 115. These TRAIL mutants were then cloned into pshuttle CMV vector.

However, neither the $^{105}$EKQQ$^{108}$ (SEQ ID NO: 16) nor the $^{105}$EKQQHISPLV$^{115}$ (SEQ ID NO: 17) deletion mutation in TRAIL (mutants 1 and 2 respectively) were capable of blocking the cleavage of the TRAIL from the cell membrane (FIG. 12). More extensive deletion mutations were not possible since these would interfere with either the functional extracellular domain or the anchoring domain of the protein. For these reasons our alternative strategy of engineering the TRAIL-CD40L fusion protein was explored.

7. Data Showing the Performance Benefits of the TRAIL Fusion Protein Compared to Anti-TRAIL-Receptor Antibodies Monoclonal antibodies targeting either TRAIL receptor 1 (Mapatumumab) or TRAIL receptor 2 (Lexatumumab) are currently being investigated in clinical trials, emphasising the importance of TRAIL as novel anti-cancer target. Because of the commercially sensitive nature of the development of these agents, it has not been possible to perform experiments to directly compare these antibodies with our TRAIL fusion protein. However, using published data, comparison of the ability of the antibodies and our fusion protein to induce apoptosis in comparable cell lines is possible. The antibodies can induce apoptosis in some cell lines. However, others are resistant to antibody alone and require combination with other agents such as cytotoxic chemotherapy to overcome this resistance. For example, Hela cells are resistant to lexatumumab unless used in combination with cisplatin (Clin Cancer Res 2009; 15: 2039-2047). In our experiments, Hela are relatively resistant to wild-type TRAIL unless administered with chemotherapy, consistent with the lexatumumab data. However, Hela are sensitive to our TRAIL fusion even when administered as a single agent, suggesting greater potency than both wild-type TRAIL and anti-TRAILR2 antibody (FIG. 13). Similarly, the liver cancer cell line, HepG2, is resistant to mapatumumab (AACR, Cancer Res 2011; 71: suppl 8: abstract nr 4097) but is highly sensitive to the TRAIL fusion (FIG. 13).

Furthermore, whilst these monoclonal antibodies target either TRAIL receptors 1 or 2, our fusion protein engages both receptors, which may facilitate a wider therapeutic spectrum.

| Sequence information |
|---|

SEQ ID NO: 1
Wild type TRAIL (underlined letters represent TRAIL sequence replaced by CD40L
sequence in the fusion protein of SEQ ID NO: 3)
MAMMEVQGGP SLGQTCVLIV IFTVLLQSLC VAVTYVYFTN ELKQMQDKYS KSGIACFLKE
DDSYWDPNDE ESMNSPCWQV KWQLRQLVRK MILRTSEETI STVQEKQQNI SPLVRERGPQ
RVAAHITGTR GRSNTLSSPN SKNEKALGRK INSWESSRSG HSFLSNLHLR NGELVIHEKG
FYYIYSQTYF RFQEEIKENT KNDKQMVQYI YKYTSYPDPI LLMKSARNSC WSKDAEYGLY
SIYQGGIFEL KENDRIFVSV TNEHLIDMDH EASFFGAFLV G SEQ ID NO: 2
Wild type CD40L (underlined letters represent CD40L sequence replaced by TRAIL
sequence in the fusion protein of SEQ ID NO: 3)
MIETYNQTSP RSAATGLPIS MKIFMYLLTV FLITQMIGSA LFAVYLHRRL DKIEDERNLH
EDFVFMKTIQ RCNTGERSLS LLNCEEIKSQ FEGFVKDIML NKEETKKENS FEMQKGDQNP
QIAAHVISEA SSKTTSVLQW AEKGYYTMSN NLVTLENGKQ LTVKRQGLYY IYAQVTFCSN
REASSQAPFI ASLCLKSPGR FERILLRAAN THSSAKPCGQ QSIHLGGVFE LQPGASVFVN
VTDPSQVSHG TGFTSFGLLK L SEQ ID NO: 3
A fusion protein of the invention (letters without underline are sequence based upon CD40L,
while underlined letters represent the TRAIL C-terminal region)
MIETYNQTSP RSAATGLPIS MKIFMYLLTV FLITQMIGSA LFAVYLHRRL DKIEDERNLH
EDFVFMKTIQ RCNTGERSLS LLNCEEIKSQ FEGFVKDIML NKEETKKEVR ERGPQRVAAH
ITGTRGRSNT LSSPNSKNEK ALGRKINSWE SSRSGHSFLS NLHLRNGELV IHEKGFYYIY
SQTYFRFQEE IKENTKNDKQ MVQYIYKYTS YPDPILLMKS ARNSCWSKDA EYGLYSIYQG
GIFELKENDR IFVSVTNEHL IDMDHEASFF GAFLVG SEQ ID NO: 4
The nucleotide sequence that encodes the fusion protein of SEQ ID NO: 3 (bases 1-324,
encoding the CD40L N-terminal, are shown without underline, while bases 325-831 bp
encoding the TRAIL C-terminal region, and corresponding to 340-846 bp from the wild type
TRAIL sequence, are underlined). Note that the final codon, ACT, is a stop codon which is
not translated.
ATGATCGAAACATACAACCAAACTTCTCCCCGATCTGCGGCCACTGGACTGCCCATCAG
CATGAAAATTTTTATGTATTTACTTACTGTTTTTCTTATCACCCAGATGATTGGGTCAGCA
CTTTTTGCTGTGTATCTTCATAGAAGGTTGGACAAGATAGAAGATGAAAGGAATCTTCAT
GAAGATTTTGTATTCATGAAAACGATACAGAGATGCAACACAGGAGAAAGATCCTTATC
CTTACTGAACTGTGAGGAGATTAAAAGCCAGTTTGAAGGCTTTGTGAAGGATATAATGT
TAAACAAGAGGAGACGAAGAAGAAGTGAGAGAAAGAGGTCCTCAGAGAGTAGCAGC
TCACATAACTGGGACCAGAGGAAGAAGCAACACATTGTCTTCTCCAAACTCCAAGAATG
AAAAGGCTCTGGGCCGCAAAATAAACTCCTGGGAATCATCAAGGAGTGGGCATTCATT
CCTGAGCAACTTGCACTTGAGGAATGGTGAACTGGTCATCCATGAAAAAGGGTTTTACT
ACATCTATTCCCAAACATACTTTCGATTTCAGGAGGAAATAAAAGAAAACACAAAGAACG
ACAAACAAATGGTCCAATATATTTACAAATACACAAGTTATCCTGACCCTATATTGTTGAT
GAAAAGTGCTAGAAATAGTTGTTGGTCTAAAGATGCAGAATATGGACTCTATTCCATCTA
TCAAGGGGGAATATTTGAGCTTAAGGAAAATGACAGAATTTTTGTTTCTGTAACAAATGA
GCACTTGATAGACATGGACCATGAAGCCAGTTTTTTCGGGGCCTTTTTAGTTGGCTAA Sequence alignment between the wild-type TRAIL sequence (query—SEQ ID NO: 5) and the TRAIL sequence used in the fusion protein (subject—SEQ ID NO: 6) is 99%. However the mismatched (TTT changed to TTC) nucleotide did not change the amino acid as the two triplet codons encode the same amino acid (Phe).

```
Query  339  AGTGAGAGAAAGAGGTCCTCAGAGAGTAGCAGCTCACATAACTGGGACCAGAGGAAGAAG  398
            ||||||||||||||||||||||||||||||||||||||||||||||||||||||||||||
Sbjct  324  AGTGAGAGAAAGAGGTCCTCAGAGAGTAGCAGCTCACATAACTGGGACCAGAGGAAGAAG  383

Query  399  CAACACATTGTCTTCTCCAAACTCCAAGAATGAAAAGGCTCTGGGCCGCAAAATAAACTC  458
            ||||||||||||||||||||||||||||||||||||||||||||||||||||||||||||
Sbjct  384  CAACACATTGTCTTCTCCAAACTCCAAGAATGAAAAGGCTCTGGGCCGCAAAATAAACTC  443

Query  459  CTGGGAATCATCAAGGAGTGGGCATTCATTCCTGAGCAACTTGCACTTGAGGAATGGTGA  518
            ||||||||||||||||||||||||||||||||||||||||||||||||||||||||||||
Sbjct  444  CTGGGAATCATCAAGGAGTGGGCATTCATTCCTGAGCAACTTGCACTTGAGGAATGGTGA  503

Query  519  ACTGGTCATCCATGAAAAAGGGTTTTACTACATCTATTCCCAAACATACTTTCGATTTCA  578
            ||||||||||||||||||||||||||||||||||||||||||||||||||||||||||||
Sbjct  504  ACTGGTCATCCATGAAAAAGGGTTTTACTACATCTATTCCCAAACATACTTTCGATTTCA  563

Query  579  GGAGGAAATAAAAGAAAACACAAAGAACGACAAACAAATGGTCCAATATATTTACAAATA  638
            ||||||||||||||||||||||||||||||||||||||||||||||||||||||||||||
Sbjct  564  GGAGGAAATAAAAGAAAACACAAAGAACGACAAACAAATGGTCCAATATATTTACAAATA  623

Query  639  CACAAGTTATCCTGACCCTATATTGTTGATGAAAAGTGCTAGAAATAGTTGTTGGTCTAA  698
            ||||||||||||||||||||||||||||||||||||||||||||||||||||||||||||
Sbjct  624  CACAAGTTATCCTGACCCTATATTGTTGATGAAAAGTGCTAGAAATAGTTGTTGGTCTAA  683
```

-continued

```
Query  699  AGATGCAGAATATGGACTCTATTCCATCTATCAAGGGGGAATATTTGAGCTTAAGGAAAA  758
            ||||||||||||||||||||||||||||||||||||||||||||||||||||||||||||
Sbjct  684  AGATGCAGAATATGGACTCTATTCCATCTATCAAGGGGGAATATTTGAGCTTAAGGAAAA  743

Query  759  TGACAGAATTTTTGTTTCTGTAACAAATGAGCACTTGATAGACATGGACCATGAAGCCAG  818
            ||||||||||||||||||||||||||||||||||||||||||||||||||||||||||||
Sbjct  744  TGACAGAATTTTTGTTTCTGTAACAAATGAGCACTTGATAGACATGGACCATGAAGCCAG  803

Query  819  TTTTTTTGGGGCCTTTTTAGTTGGCTAA                                  846
            ||||||  ||||||||||||||||||||
Sbjct  804  TTTTTTCGGGGCCTTTTTAGTTGGCTAA                                  831
```

% of identity between wild type TRAIL amino acid
sequence (query—SEQ ID NO: 7) and TRAIL mutant
sequence (subject—SEQ ID NO: 7) 100%

```
Query    1  VRERGPQRVAAHITGTRGRSNTLSSPNSKNEKALGRKINSWESSRSGHSFLSNLHLRNGE   60
            VRERGPQRVAAHITGTRGRSNTLSSPNSKNEKALGRKINSWESSRSGHSFLSNLHLRNGE
Sbjct    1  VRERGPQRVAAHITGTRGRSNTLSSPNSKNEKALGRKINSWESSRSGHSFLSNLHLRNGE   60

Query   61  LVIHEKGFYYIYSQTYFRFQEEIKENTKNDKQMVQYIYKYTSYPDPILLMKSARNSCWSK  120
            LVIHEKGFYYIYSQTYFRFQEEIKENTKNDKQMVQYIYKYTSYPDPILLMKSARNSCWSK
Sbjct   61  LVIHEKGFYYIYSQTYFRFQEEIKENTKNDKQMVQYIYKYTSYPDPILLMKSARNSCWSK  120

Query  121  DAEYGLYSIYQGGIFELKENDRIFVSVTNEHLIDMDHEASFFGAFLVG             168
            DAEYGLYSIYQGGIFELKENDRIFVSVTNEHLIDMDHEASFFGAFLVG
Sbjct  121  DAEYGLYSIYQGGIFELKENDRIFVSVTNEHLIDMDHEASFFGAFLVG             168
```

The invention claimed is:

1. A fusion protein comprising an apoptosis-inducing amino acid sequence comprising the extracellular domain of TRAIT or an apoptosis-inducing fragment thereof, and a membrane-anchoring amino acid sequence comprising the transmembrane domain of CD40L or a membrane-anchoring fragment thereof,
    wherein the apoptosis-inducing amino acid sequence and the membrane-anchoring amino acid sequence are each in orientation such that the fusion protein is capable of anchoring in a cell membrane and inducing apoptosis.

2. The fusion protein according to claim 1, wherein the apoptosis-inducing amino acid sequence consists of the extracellular domain of TRAIL.

3. The fusion protein according to claim 1, wherein the fragment comprises about 165, 160, 155, or 150 contiguous amino acid residues of the native TRAIL sequence.

4. The fusion protein according to claim 1, wherein the fusion protein comprises amino acid residues from 109 to 276 of SEQ ID NO: 3.

5. The fusion protein according to claim 1, comprising amino acids residues 1 to 108 of SEQ ID NO: 3.

6. The fusion protein according to claim 1, comprising or consisting of the amino acid sequence set out in SEQ ID NO: 3.

7. A polynucleotide encoding a fusion protein according to claim 1.

8. The polynucleotide according to claim 7, wherein the polynucleotide comprises the sequence set out in SEQ ID NO: 4.

* * * * *

UNITED STATES PATENT AND TRADEMARK OFFICE
CERTIFICATE OF CORRECTION

PATENT NO. : 10,370,422 B2  
APPLICATION NO. : 15/304282  
DATED : August 6, 2019  
INVENTOR(S) : Daniel Palmer and Taha Elmitwalli Page 1 of 1

It is certified that error appears in the above-identified patent and that said Letters Patent is hereby corrected as shown below:

In the Claims

Claim 1, Column 29 Line 54 replace "TRAIT" with "TRAIL".

Signed and Sealed this  
Eleventh Day of February, 2020

Andrei Iancu  
*Director of the United States Patent and Trademark Office*